United States Patent
Prosl et al.

(10) Patent No.: US 9,295,773 B2
(45) Date of Patent: Mar. 29, 2016

(54) HEMODIALYSIS ACCESS SYSTEM

(76) Inventors: Frank Prosl, Duxbury, MA (US);
Hans-Dietrich Polaschegg, Koestenberg (AT); Heidrun Polaschegg, legal representative, Koestenberg (AU)

( * ) Notice: Subject to any disclaimer, the term of this patent is extended or adjusted under 35 U.S.C. 154(b) by 83 days.

(21) Appl. No.: 13/884,115

(22) PCT Filed: Nov. 9, 2011

(86) PCT No.: PCT/US2011/060045
§ 371 (c)(1),
(2), (4) Date: Sep. 26, 2013

(87) PCT Pub. No.: WO2012/064881
PCT Pub. Date: May 18, 2012

(65) Prior Publication Data
US 2014/0024998 A1    Jan. 23, 2014

Related U.S. Application Data

(60) Provisional application No. 61/411,537, filed on Nov. 9, 2010.

(51) Int. Cl.
*A61M 5/00* (2006.01)
*A61M 1/36* (2006.01)

(52) U.S. Cl.
CPC ........... *A61M 1/3653* (2013.01); *A61M 1/3655* (2013.01); *A61M 1/3661* (2014.02)

(58) Field of Classification Search
CPC A61M 1/3653; A61M 1/3655; A61M 1/3661
See application file for complete search history.

(56) References Cited

U.S. PATENT DOCUMENTS

| | | | |
|---|---|---|---|
| 3,731,681 | A | 5/1973 | Blackshear et al. |
| 4,014,328 | A | 3/1977 | Cluff et al. |
| 4,190,040 | A | 2/1980 | Schulte |
| 4,258,711 | A | 3/1981 | Tucker et al. |
| 4,337,251 | A | 6/1982 | Pfirrmann |

(Continued)

FOREIGN PATENT DOCUMENTS

| | | |
|---|---|---|
| EP | 1 442 753 A1 | 4/2004 |
| WO | WO 01/32141 | 5/2001 |

OTHER PUBLICATIONS

Masumoto et al., Usefulness of Exchanging a Tunneled Central Venous Catheter Using a Subcutaneous Fibrous Sheath, Nutrition, 2010, pp. 1-4.

(Continued)

*Primary Examiner* — Leslie Deak
(74) *Attorney, Agent, or Firm* — Pandiscio & Pandiscio

(57) ABSTRACT

A medical blood access system used for hemodialysis treatment to enable blood withdrawal for processing of blood by an external apparatus and return the same blood to a patient, comprising an interfacial fluid conduit between the machine and patient's blood supply which is repeatedly connectable along a guided pathway passing through epidermis and subcutaneous tissue via a naturally formed tissue tract to enter blood space, providing improved patient safely, convenience, effective prophylaxis, without bleeding or tissue trauma or pain, and is executable by the patient to precisely connect and disconnect with minimal disfigurement or life restrictions, and is useable on virtually all patients soon after placement and is robust and safe to high blood flow.

21 Claims, 12 Drawing Sheets

(56) References Cited

U.S. PATENT DOCUMENTS

| | | | |
|---|---|---|---|
| 4,400,169 | A | 8/1983 | Stephen |
| 4,417,888 | A | 11/1983 | Cosentino et al. |
| 4,445,896 | A | 5/1984 | Gianturco |
| 4,490,137 | A | 12/1984 | Moukheibir |
| 4,496,343 | A | 1/1985 | Prosl et al. |
| 4,543,088 | A | 9/1985 | Bootman et al. |
| 4,569,675 | A | 2/1986 | Prosl et al. |
| 4,581,020 | A | 4/1986 | Mittleman |
| 4,673,394 | A | 6/1987 | Fenton, Jr. et al. |
| 4,692,146 | A | 9/1987 | Hilger |
| 4,704,103 | A | 11/1987 | Stober et al. |
| 4,710,167 | A | 12/1987 | Lazorthes |
| 4,710,174 | A | 12/1987 | Moden et al. |
| 4,777,698 | A | 10/1988 | Lord |
| 4,781,680 | A | 11/1988 | Redmond et al. |
| 4,781,695 | A | 11/1988 | Dalton |
| 4,790,826 | A | 12/1988 | Elftman |
| 4,832,054 | A | 5/1989 | Bark |
| 4,857,053 | A | 8/1989 | Dalton |
| 4,978,338 | A | 12/1990 | Melsky et al. |
| 5,041,098 | A | 8/1991 | Loiterman et al. |
| 5,057,084 | A | 10/1991 | Ensminger et al. |
| 5,092,849 | A | 3/1992 | Sampson |
| 5,180,365 | A | 1/1993 | Ensminger et al. |
| 5,226,879 | A | 7/1993 | Ensminger et al. |
| 5,281,199 | A | 1/1994 | Ensminger et al. |
| 5,318,545 | A | 6/1994 | Tucker |
| 5,336,194 | A | 8/1994 | Polaschegg et al. |
| 5,350,360 | A | 9/1994 | Ensminger et al. |
| 5,356,381 | A | 10/1994 | Ensminger et al. |
| 5,417,656 | A | 5/1995 | Ensminger et al. |
| 5,476,451 | A | 12/1995 | Ensminger et al. |
| 5,503,630 | A | 4/1996 | Ensminger et al. |
| 5,520,643 | A | 5/1996 | Ensminger et al. |
| 5,527,277 | A | 6/1996 | Ensminger et al. |
| 5,527,278 | A | 6/1996 | Ensminger et al. |
| 5,531,684 | A | 7/1996 | Ensminger et al. |
| 5,704,915 | A | 1/1998 | Melsky et al. |
| 5,755,780 | A | 5/1998 | Finch, Jr. et al. |
| 5,911,706 | A | 6/1999 | Estabrook et al. |
| 5,954,691 | A | 9/1999 | Prosl |
| 5,989,206 | A | 11/1999 | Prosl et al. |
| 5,989,239 | A | 11/1999 | Finch et al. |
| 6,007,516 | A | 12/1999 | Burbank et al. |
| 6,013,058 | A | 1/2000 | Prosl et al. |
| 6,120,492 | A | 9/2000 | Finch et al. |
| 6,166,007 | A | 12/2000 | Sodemann |
| 6,206,851 | B1 | 3/2001 | Prosl |
| 6,350,251 | B1 | 2/2002 | Prosl et al. |
| 6,352,521 | B1 | 3/2002 | Prosl |
| 6,436,084 | B1 | 8/2002 | Finch et al. |
| 6,436,089 | B1 | 8/2002 | Danielson et al. |
| 6,451,003 | B1 | 9/2002 | Prosl et al. |
| 7,131,962 | B1 | 11/2006 | Estabrook et al. |
| 2003/0144362 | A1 | 7/2003 | Utterberg et al. |
| 2003/0175323 | A1 | 9/2003 | Utterberg et al. |
| 2004/0156908 | A1 | 8/2004 | Polaschegg |
| 2004/0199126 | A1 | 10/2004 | Harding et al. |
| 2005/0042240 | A1 | 2/2005 | Utterberg et al. |
| 2005/0209573 | A1 | 9/2005 | Brugger et al. |
| 2006/0024372 | A1 | 2/2006 | Utterberg et al. |
| 2008/0027043 | A1 | 1/2008 | Herdeis et al. |
| 2008/0177217 | A1 | 7/2008 | Polaschegg |
| 2009/0036872 | A1 | 2/2009 | Fitzgerald et al. |
| 2009/0209918 | A1 | 8/2009 | Berglund |
| 2010/0106102 | A1 | 4/2010 | Ziebol et al. |

OTHER PUBLICATIONS

Yee, There's No Place Like Home, Advances in Chronic Kidney Disease, 2009, vol. 16, No. 3, pp. 156-157.
Abdelwhab et al., Pulmonary Hypertension in Chronic Renal Failure Patients, American Journal of Nephrology, 2008, vol. 28, pp. 990-997.
Agarwal, Systemic Effects of Hemodialysis Access, Advances in Chronic Kidney Disease, 2015, vol. 22, No. 6, pp. 459-465.
Asch et al., Effect of Financial Incentives to Physicians, Patients, or Both on Lipid Levels a Randomized Clinical Trial, The Journal of the American Medical Association, 2015, vol. 314, No. 18, pp. 1926-1935.
Depner et al., Hemodialysis Adequacy 2006, American Journal of Kidney Disease, 2006.
El-Khatib et al., Role of C-Reactive Protein, Reticulocyte Haemoglobin Content and Inflammatory Markers in Iron and Erythropoietin Administration in Dialysis Patients, Nephrology, 2006, vol. 11, pp. 400-404.
Fontsere et al., Lock Tunneled Catheters with Taurolidine-Citrate-Heparin Lock Solution Significantly Improves Inflammatory Profile in Hemodialysis Patients, Antimicrobial Agents and Chemotherapy, 2014, vol. 58, No. 7, pp. 4180-4184.
Hawley et al., Complications of Home Hemodialysis, Hemodialysis International, 2008, vol. 12, pp. S21-S25.
Iwashima et al., Effects of the Creation of Arteriovenous Fistula for Hemodialysis on Cardiac Function and Natriuretic Peptide Levels in CFR, American Journal of Kidney Diseases, 2002, vol. 40, No. 5, pp. 974-982.
Al-Jaishi et al., Patency Rates of the Arteriovenous Fistula for Hemodialysis: A Systematic Review and Meta-analysis, American Journal of Kidney Disease, 2014, vol. 63, No. 3, pp. 464-478.
Allon, Prophylaxis Against Dialysis Catheter-Related Bacteremia with a Novel Antimicrobial Lock Solution, Clinical Infectious Diseases, 2003, vol. 36, pp. 1539-1544.
Amerling, Con: On Cardiovascular Outcomes and the Arteriovenous Fistula: Lesser of Evils, Nephrol. Dial. Transplant, 2012, vol. 27, pp. 3756-3757.
Blake et al., The Risks of Vascular Access, Kidney International, 2012, vol. 82, pp. 623-625.
Classen et al., Specialty Society Clinical Practice Guidelines Time for Evolution or Revolution?, The Journal of the American Medical Association, 2015.
Foley et al., Early Mortality in Patients Starting Dialysis Appears to Go Unregistered, Kidney International, 2014, vol. 86, pp. 392-398.
Gomes et al., Re-envisioning Fistula First in a Patient-Centered Culture, Clinical Journal of the American Society of Nephrology, 2013, vol. 8(10), pp. 1791-1797.
Karkar et al., Benefits and Implementation of Home Hemodialysis: A Narrative Review, Saudi Journal of Kidney Diseases and Transplantation, 2015, vol. 26(6), pp. 1095-1107.
Kraus et al., A comparison of center-based vs. homebased daily hemodialysis for patients with end-stage renal disease, Hemodialysis International, 2007, vol. 11, pp. 468-477.
Lehman, Richard, Richard Lehman's Journal Review, The BMJ, 2015, vol. 373.
Ridao-Cano et al., Vascular Access for Dialysis in the Elderly, Blood Purification, 2002, vol. 20, pp. 563-568.
Polaschegg, Hans-Dietrich, Catheter Locking Solution Spillage:Theory and Experimental Verification, Blood Purification, 2008, vol. 26, pp. 255-260.
Polaschegg, Hans-Dietrich, Venous Needle Dislodgement: The Pitfalls of Venous Pressure Measurement and Possible Alternatives, A Review, Journal of Renal Care, 2010, vol. 36(1), pp. 41-48.
Polaschegg, Hans-Dietrich, Dialysis Times, 2000, vol. 7, No. 2.
Ori et al., The Contribution of an Arteriovenous Access for Hemodialysis to Left Ventricular Hypertrophy, American Journal of Kidney Diseases, 2002, vol. 40, No. 4, pp. 745-752.
Movilli et al., Long-term Effects of Arteriovenous Fistula Closure on Echocardiographic Functional and Structural Findings in Hemodialysis Patients: A Prospective Study, American Journal of Kidney Diseases, 2010, vol. 55, No. 4, pp. 682-689.
Moore et al., Comparative Effectiveness of Two Catheter Locking Solutions to Reduce Catheter-Related Bloodstream Infection in Hemodialysis Patients, Clinical Journal of The American Society of Nephrology, 2014, vol. 9, pp. 1-8.
Mermel, Leonard A., What is the evidence for intraluminal colonization of hemodialysis catheters?, International Society of Nephrology, 2014, pp. 1-6.

(56) References Cited

OTHER PUBLICATIONS

Niederhuber et al., Totally Implanted Venous and Arterial Access System to Replace External Catheters in Cancer Treatment, Surgery, 1982, vol. 92, No. 4, pp. 706-712.
Brothers et al., Experience with Subcutaneous Infusion Ports in Three Hundred Patients, Surg. Gynecol. Obstet., 1988, vol. 166, No. 4, pp. 295-301.
Field et al., Primary Patency Rates of AV Fistulas and the Effect of Patient Variables, The Journal of Vascular Access, 2008, vol. 9, No. 1, pp. 45-50.
Allon, Michael, Prophylaxis against Dialysis Catheter-Related Bacteremia with a Novel Antimicrobial Lock Solution, Clinical Infectious Diseases, Jun. 15, 2003, pp. 1539-1544.
Ash, Stephen R., Advances in Tunneled Central Venous Catheters for Dialysis: Design and Performance, Semin Dial. 2008, pp. 504-515.
Ayus, JC et al., Phosphorus balance and mineral metabolism with 3 hour daily hemodialysis, Kidney Int. 2007, pp. 336-334.
Boorgu, R. et al., Adjunctive Antibiotic/Anticoagulant Lock Therapy in the Treatment of Bacteremia . . . , ASAIO Journal, 2000, pp. 767-770, vol. 46, Issue 6.
Boss, Willem Jan W., et al., Effects of arteriovenous fistulas on cardiac oxygen supply and demand, Kidney Int., 1999, pp. 2049-2053, vol. 55.
Breidthardt, Tobias et al., Dialysis-Induced Myocardial Stunning: The Other Side of the Cardiorenal Syndrome, Reviews in Cardiovascular Medicine, Jan. 2011, vol. 12, No. 1.
Brouwer, Deborah J., Cannulation Camp: Basic Needle Cannulation Training for Dialysis Staff, Dialysis & Transplantation, 1995, pp. 606-612, vol. 24, No. 11.
Buerger, Thomas et al., Implantation of a new device for haemodialysis, Nephrology Dialyis Transplantation, 2000, pp. 722-724.
Chan, Christopher T., Cardiovascular effects of home intensive hemodislysis, Advances in Chronic Kidney Disease, May 2009, pp. 173-178, vol. 16, No. 3.
Chan, Christopher T. et al., Improvement in exercise duration and capacity after conversion to nocturnal home haemodialysis. Nephrol. Dial. Transplantation, 2007, pp. 3285-3291.
Chazot, Charles et al., The advantages and challenges of increasing the duration and frequency of maintenance dialysis sessions, Nat. Clin. Pract. Nephrol., 2009, pp. 34-44.
Cohen, Alfred M. et al., Treatment of hepatic metastases by transaxillary hepatic artery chemotherapy using an implanted drug pump, Cancer, 1983, pp. 2013-2019, vol. 51, No. 11.
Culleton, Bruce F. et al., The impact of short daily and nocturnal hemodialysis on quality of life, cardiovascular risk and survival, J. Nephrol., Jun. 2011, pp. 405-415.
Desmeules Simon et al., Venous access for chronic hemodialysis: "undesirable yet unavoidable", Artificial Organs, 2004; pp. 611-616.
Dewan P A et al., Plastic migration from implanted centeral venous access devices, Arch. Dis. Child. 1999, pp. 71-72.
Egbert, Jan Oliver Ten Hallers, Accessory Device Fixation for Voice Rehabilitation in Laryngectomised Patients, PhD Thesis, University Medical Center Groningen, ND, 2006.
Goldstein Stuart L. et al., Non-infected hemodialysis catheters are associated with increased inflammation compared to AVF, Kidney Int., Aug. 12, 2009, pp. 1063-1069.
Gotch, Frank A. et al., A mechanistic analysis of the National Cooperative Dialysis Study (NCDS), Kidney Int., 1985, pp. 526-534, vol. 28.
Greenhalgh J. et al., Drug-eluting stents versus bare metal stents for angina or acute coronary syndromes, Cochrane Database Syst Rev., May 12, 2010.
Gura Victor et al., Technical Breakthroughs in the Wearable Artificial Kidney(WAK), Clin. J. Am, Soc. Nephrol., 2009, pp. 1441-1448, vol. 4.
Hanly Patrick, Sleep disorders and home dialysis, Advances in Chronic Kidney Disease 2009, pp. 179-188, vol. 16, No. 3.

Hodges Timothy C. et al., Longitudinal comparison of dialysis access methods: risk factors for failure. J. of Vascular Surgery, Dec. 1997, pp. 1009-1019, vol. 26, No. 6.
Home Hemodialysis Fact Sheet, American Nephrology Nurse's Association, 2007, www.annanurse.org.
Huijbregts, Henricus J.T. et al.; Hemodialysis Arteriovenous Fistula Patency Revisited: Results of a Prospective, Multicenter . . . , Clin. J. Am. Soc. Nephrol., 2008, pp. 714-719.
Johansen, Kristen L. et al., Survival and hospitalization among patients using nocturnal and short daily compared to conventional . . . , Kidney Int., 2009, pp. 984-990.
Kheda, Mufaddal F. et al., Influence of arterial elasticity and vessel dilatation on arteriovenous fistula maturation. . . , Nephrol. Dial. Transplant., 2010, pp. 525-531.
Konner, Klaus, History of vascular access for haemodialysis, Nephrol. Dial. Transplant., 2005, pp. 2629-2635.
Levin, Nathan W. et al., New access device for hemodialysis . . . ASAIO Journal, 19984, pp. M529-M531, 1984.
Maya Ivan D. et al., Outcomes of brachiocephalic fistulas, transposed brachiobasilic fistulas, and upper arm grafts, Clin. J. Am. Soc. Nephrol., 2009, pp. 86-92. vol. 4.
Miller, Jessica E. et al., Association of hemodialysis treatment time and dose with mortality and the role of . . . , Am. J. Kidney, Dis., Jan. 2010, pp. 100-112, vol. 55, No. 1.
Nakhoul, Farid et al., The pathogenesis of pulmonary hypertension in haemodialysis patients via arterio-venous access. Nephrol. Dial. Transplant., 2005, pp. 1686-1692.
Parker III, Thomas F. et al., Conclusions, Consensus, and Directions for the Future, Clin. J. Am. Soc. Nephrol., 2009, pp. S139-S144.
Pauly, Robert P., Nocturnal home hemodialysis and short daily hemodialysis compared with kidney . . . , Adv. Chronic Kidney Dis., May 2009, pp. 169-172, vol. 16, No. 3.
Peterson, William J. et al., Disparities in fistula maturation persists despite preoperative vascular mapping, Clin. J. Am. Soc. Nephrol., 2008, pp. 437-441.
Pierratos, Andreas, Daily nocturnal hemodialysis—a paradigm shift worthy of disrupting current dialysis practice, Nat. Clin. Pract. Nephrol., 2008, pp. 602-603, vol. 4, No. 11.
Polaschegg, Hans-Dietrich, Loss of Catheter Locking Solution Caused by Fluid Density, ASAIO Journal, 2005, pp. 220-225.
Rastogi, Anjay et al., Technological Advances in Renal Replacement Therapy: Five Years and Beyond, Clin. J. Am. Soc. Nephrol., 2009, pp. S132-S136.
Ross, John J. et al., Infections Associated with Use of the LifeSite Hemodialysis Access System, Clinical Infectious Diseases, Jul. 1, 2002, pp. 93-95.
Scribner, Belding H. et al., The Hemodialysis Product (HDP): A Better Index of Dialysis Adequacy than KT/V, Dialysis and Transplantation, 2002, pp. 431-433, vol. 31, No. 1.
Singh-Ranger, Gurpreet et al., Capsular contraction following immediate reconstructive surgery for breast cancer . . . , International Seminars in Surgical Oncolcay, 2004.
Twardowski, Zyblut, Commentary on Verhallen AM et al. (2007) Cannulating hemodialysis . . . , Nat. Clin. Pract. Nephrol. Dec. 2007, pp. 648-649, vol. 3., No. 12.
Weber, Catherine L. et al., Outcomes of vascular access creation prior to dialysis: budding the case for early referral, ASAIO Journal, 2009, pp. 355-360.
Malhotra et al., Decompensated High-Output Congestive Heart Failure in a Patient with AVF and the Role of Right Heart Catheterization: A Case Study, Hemodialysis International, 2012, vol. 16, pp. S58-S61.
Richard et al., Negotiating Living with an Arteriovenous Fistula for Hemodialysis, Nephrology Nursing Journal, 2010, vol. 37, No. 4, pp. 363-375.
Sandroni, Venous Needle Dislodgement During Hemodialysis: An Unresolved Risk of Catastrophic Hemorrage, Hemodialysis International, 2005, vol. 9, No. 1, pp. 102-103.
Savage et al., The Impact of Arteriovenous Fistula Formation on Central Hemodynamic Pressures in Chronic Renal Failure Patients: A Prospective Study, American Journal of Kidney Diseases, 2002, vol. 40, No. 4. pp. 753-759.

(56) References Cited

OTHER PUBLICATIONS

Sodemann et al., Two Years' Experience with Dialock and CLS (A New Antimicrobial Lock Solution), Blood Purification, 2001, vol. 19, pp. 251-254.

Van Eps et al., The Impact of Extended-Hours Home Hemodialysis and Buttonhole Cannulation Technique on Hospitalization Rates for Septic Events Related to Dialysis Access, Hemodialysis International, 2010, vol. 14, pp. 451-463.

Van Loon et al., Cannulation Practice Patterns in Haemodialysis Vascular Access: Predictors for Unsuccessful Cannulation, Journal of Renal Care, 2009.

HEMODIALYSIS ACCESS SYSTEM

REFERENCE TO PENDING PRIOR PATENT APPLICATION

This patent application claims benefit of pending prior U.S. Provisional Patent Application Ser. No. 61/411,537, filed Nov. 9, 2010 by Frank Prosl et al. for HEMODIALYSIS ACCESS SYSTEM, which patent application is hereby incorporated herein by reference.

FIELD OF THE INVENTION

This invention relates to blood access methods and apparatus for use in the replacement of kidney function necessitated by the failure of natural kidney function, which is sometimes referred to as end stage renal disease (ESRD). More particularly, the present invention relates to hemodialysis systems designed for operation and maintenance by an unaided patient for recurring treatment in the patient's home. The present invention also relates to blood access methods for the treatment of congestive heart failure or hyperlipidemia. In general, these blood treatment methods include, but are not limited to, hemodialysis, hemofiltration, hemodiafiltration, plasmapheresis, ultrafiltration, aquapheresis, n lipid pheresis and hemoperfusion. In the following description, the term "hemodialysis" (or "HD") is generally used in connection with the present invention, but it is not intended to restrict the use of the device and methods of the present invention to hemodialysis, i.e., the present invention may be used for other blood treatment methods or drug infusion.

BACKGROUND OF THE INVENTION

End stage renal disease (ESRD) is an irreversible condition of kidney failure which results in death without medical intervention. The current standard (i.e., most common) U.S. medical care for ESRD is to replace kidney function with repeated extracorporeal blood processing called hemodialysis (HD). ESRD affects more than one million people world-wide and is increasing. Around 1963, long term HD treatments became possible with the introduction of the "Scribner Shunt", which enables repeated access to a patient's central blood supply. Doctors experimented with time and frequency of HD and, by the 1970s, many doctors were using 3 treatments per week, with a treatment time of approximately 5 hours (or longer) per treatment. Although it was believed that a patient's well-being depended on limiting toxin exposure, safe values for such exposure were never elucidated.

In the 1980s, a mathematical relationship called "Kt/V" was derived by Dr. Gotch, which may be used to quantify toxin removal during HD treatment. Blood urea was selected as a representative biochemical marker for toxins, since blood urea was removed during HD and is easy measure (although blood urea itself is not a toxin). (Gotch F A, Sargent J A. A mechanistic analysis of the National Cooperative Dialysis Study (NCDS) Kidney Int 1985; 28:526-534) Trials comparing clinical outcomes to Kt/V led to agreed Kt/V levels for defining adequate treatment. Kt/V is a number calculated for each patient from the urea clearance characteristics of their HD dialyzer (K), the dialysis treatment time (t) and volume of blood treated (V). Kt/V values became the key marker to quantify US HD treatment and to justify the standard of three HD sessions per week (National Kidney Foundation. KDOQI). Clinical Practice Guidelines and Clinical Practice Recommendations for 2006 Updates: Hemodialysis Adequacy. Am J Kidney Dis 2006; 48:S3-S90; Miller J E, Kovesdy C P, Nissenson A R, Mehrotra R, Streja E, Van Wyck D, Greenland S, Kalantar-Zadeh K. Association of hemodialysis treatment time and dose with mortality and the role of race and sex. Am J Kidney Dis 2010; 55:100-12)

Some doctors voiced misgivings that the Kt/V value was used as a comprehensive or determinative marker of HD performance; and therefore for measuring/evaluating patient health and quality of life. Adopting Kt/V criteria to determine "adequate" HD treatment for more than 2 decades has permitted poor patient outcomes to continue without meaningful improvements. Most patients are subject to frequent complications and poor quality of life, without rehabilitation, after beginning dialysis. Not surprisingly, many U.S. patients choose to stop HD and die.

Over time many studies have described deficiencies in Kt/V as an objective measure for achieving good health and quality of life. (Scribner, Oreopoulos. The Hemodialysis Product (HDP): A Better Index of Dialysis Adequacy than KT/V Dialysis and Transplantation 2002. 31:1) Standardized Kt/V values could be reached with regimes for most patients consisting of 3 hours of treatment administered 3 times per week. However, not all doctors agreed—some felt that longer HD sessions, and/or more frequent (i.e., daily) dialysis, would be better. Longer and more frequent dialysis is sometimes referred to as "intensive HD" (IHD). Over 2 decades IHD results show an array of improved patient outcomes including better cognitive and physical function, more restful sleep, increased appetite, less diet and fluid restrictions, increased physical activity and endurance, a reduction in drug consumption and patients reporting substantially better quality of life. (Parker T F, Glassock R J, Steinman T I. Conclusions, Consensus, and Directions for the Future. Clin J Am Soc Nephrol 2009; 4:S139-44; Chazot C, Jean G. The advantages and challenges of increasing the duration and frequency of maintenance dialysis sessions. Nat Clin Pract Nephrol 2009; 5:34-44; Pauly R P. Nocturnal home hemodialysis and short daily hemodialysis compared with kidney transplantation: emerging data in a new era. Adv Chronic Kidney Dis 2009; 16:169-72; Hanly P. Sleep disorders and home dialysis. Adv Chronic Kidney Dis 2009; 16:179-88/Chan C T. Cardiovascular effects of home intensive hemodialysis. Adv Chronic Kidney Dis 2009; 16:173-8; Johansen K L, Zhang R, Huang Y, Chen S C, Blagg C R, Goldfarb-Rumyantzev A S, Hoy C D, Lockridge R S Jr, Miller B W, Eggers P W, Kutner N G. Survival and hospitalization among patients using nocturnal and short daily compared to conventional hemodialysis: a USRDS study. Kidney Int 2009; 76:984-90; Pierratos A. Daily nocturnal hemodialysis—a paradigm shift worthy of disrupting current dialysis practice. Nat Clin Pract Nephrol 2008; 4:602-3; Chan C T, Notarius C F, Merlocco A C, Floras J. Improvement in exercise duration and capacity after conversion to nocturnal home haemodialysis. Nephrol Dial Transplant 2007; 23:3285-91; Kraus M, Burkart J, Hegeman R, Solomon R, Coplon N, Moran J. A comparison of center-based vs. home-based daily hemodialysis for patients with end-stage renal disease. Hemodial Int 2007; 11:468-77; Ayus J C, Achinger S G, Mizani M R, Chertow G M, Furmaga W, Lee S, Rodriguez F. Phosphorus balance and mineral metabolism with 3 hour daily hemodialysis. Kidney Int 2007; 71:336-42).

However, IHD performed in HD clinics imposes even greater hardship on patients than does the current treatment regimen of 3 sessions per week, each of approximately 3½ hours per session (i.e., the current HD standard treatment). IHD performed at home allows flexible scheduling, and even HD while sleeping, which is more appropriate for long term chronic therapy.

Two different IHD methods have shown superior suitability and benefit for home treatment: nocturnal HD, which is performed nearly daily during sleeping and at lower blood flow rates, and daily HD, with short duration treatment while relaxing (i.e., reading, watching TV, etc). Another potential IHD treatment could be HD performed with small, portable and fully contained HD machines (i.e., called "Wearable HD Machines") which allow a patient to dialyze almost anywhere while engaging in many activities. These "Wearable HD Machines" are in development, with several patents and papers published. (Rastogi A, Nissenson A R. Technological Advances in Renal Replacement Therapy: Five Years and Beyond. Clin J Am Soc Nephrol 2009; 4:S132-6; Gura V, Macy A S, Beizai M, Ezon C, Golper T A. Technical Breakthroughs in the Wearable Artificial Kidney (WAK). Clin J Am Soc Nephrol 2009; 4:1441-8).

One U.S. company (NextStage) is producing HD machines for the home treatment and is used by about 6000 home patients. Patients receiving IHD consistently report better quality of life.

HD is an extracorporeal blood cleansing treatment comprising the withdrawal of blood in a continuous process, the passing of the blood through a dialysis machine to remove waste products (i.e., water and metabolic toxins), and the returning of the blood back to patient. In HD clinics, senior nurses perform the blood accessing (i.e., the coupling of the machine to the patient's blood supply via the conduit interface connection called "blood access"). These blood accesses are subject to frequent complications resulting in frequent hospitalization and death. A particularly harmful failure mode is a break in the return blood line, which may result in bleedout and death of the patient if the blood loss by the patient is not stopped within a few minutes. These events still occur in HD clinics with close proximity to patients and workers. (Sandroni S. Venous needle dislodgement during hemodialysis: An unresolved risk of catastrophic hemorrhage. Hemodial Int 2005; 9:102-3; Polaschegg H D. Venous needle dislodgement: the pitfalls of venous pressure measurement and possible alternatives, a review. J Ren Care 2010; 36:41-8; MAUDE (Manufacturer and User Facility Device Experience, published by the US Food and Drug Administration—FDA) reports 2006 No. 716890, 743749, 770460, 770507.

Home-based dialysis requires patient responsibility for performing treatment including accessing of the patient's own bloodstream. It is evident that self-dialysis presents higher risk to the patient, especially from needle dislodgement, e.g., from an AV Fistula (AVF), while the patient sleeping. (FDA Advisory—Brief Summary from the Gastroenterology and Urology Devices Panel. http://www.fda.gov/AdvisoryCommittees/CommitteesMeetingMaterials/Medical Devices/MedicalDevicesAdvisoryCommittee/Gastroenterology-UrologyDevicesPanel/ucm124734.htm; Hawley C M, Jeffries J, Nearhos J, Van Eps C. Complications of home hemodialysis. Hemodial Int 2008; 12:S21-5).

Patient surveys describe considerable fear since they are aware of and/or have personally experienced failures with current access options. Such surveys also describe a patient's sense of being stigmatized by the disfigurement necessitated by HD access. Furthermore, self-accessing, which allows for greater independence and self-reliance, is an important factor in achieving broad acceptance of home HD treatment. However, fundamental improvements have not yet occurred which would provide safer, more robust and less disfiguring accessing, and which patients may perform by themselves.

The present invention is a system which solves or improves upon the current state of the art in HD access and is especially suited for home HD.

Description of Prior Blood Access Methods

Prior art ports and currently used HD blood access methods are described in various publications. (Konner K. History of vascular access for haemodialysis. Nephrol Dial Transplant 2005; 20:2629-35; Ash SR. Advances in Tunneled Central Venous Catheters for Dialysis: Design and Performance. Semin Dial 2008; 21:504-15; Desmeules S, Canaud B. Venous access for chronic hemodialysis: "undesirable yet unavoidable". Artif Organs 2004; 28:611-6; Richard T. Hemodialysis access without a shunt or catheter: the circulating port. J Vasc Access 2007; 8:86-90; Buerger T, Gebauer T, Meyer F, Halloul Z. Implantation of a new device for haemodialysis. Nephrol Dial Transplant 2000; 15:722-724; Levin N W, Yang P M, Hatch D A, Dubrow A J, Caraiani N S, Ing T S, Gandhi V C, Alto A, Davila S M, Prosl F R, Polaschegg H D, Megerman J. New access device for hemodialysis. ASAIO J 1998; 44:M529-31). Various prior art access methods will hereinafter be discussed.

Port Apparatus

The Biolink Dialock HD Port and Vasca Lifesite HD Port patents are incorporated herein by reference, as well as various configurations and arrangements of needles. FIGS. 1-4 show prior art Dialock HD port devices (U.S. Pat. No. 7,131,962, Estabrook, Port Device for Subcutaneous Access to the Vascular System of a Patient). These prior HD ports were designed for subcutaneous placement, preferably in a patient's chest region for accessing with needles connected to standard bloodlines which are attached to an HD machine.

Vascular Access Ports

Totally implantable ports for drug delivery were first used in patients around 1980. The idea of using a small implanted port for drug administration resulted from several serendipitous events. A surgeon seeking a better method to repeatedly inject drugs into the spinal space sought to implant a large infusion pump having a "side port" attachment. The pump manufacturer instead suggested that a side port alone might be better. The surgeon agreed, and this became the first chemotherapy vascular access port. The pump's side port was early used to enable angiographic detection of catheter tip position, and later was found useful for instilling additional chemotherapy drugs.

Even earlier, the pump's sideport was incorporated into an insulin pump so as to enable injection of a bolus mealtime supplement to the continuous basil insulin infusion. (Prosl U.S. Pat. No. 4,496,343; Cohen A M, Greenfield A, Wood W C, Waltman A, Novelline R, Athanasoulis C, Schaeffer N J. Treatment of hepatic metastases by transaxillary hepatic artery chemotherapy using an implanted drug pump. Cancer. 1983 Jun. 1; 51(11):2013-9 and U.S. Pat. No. 4,258,711, 1981; Niederhuber J E, Ensminger W, Gyves J W, Liepman M, Doan K, Cozzi E. Totally implanted venous and arterial access system to replace external catheters in cancer treatment. Surgery 1982 October; 92(4):706-12).

Chemotherapy ports found wide acceptance, since such ports offered better care than catheters or needle punctures for repeatedly accessing blood sites. The improvements were: (1) a fast and easy method to access blood vessels, (2) lower complications due to infection and/or thrombosis, (3) patient appreciation of the lesser obtrusiveness when compared to catheters, and better patient self-image, and (4) simplified implantation with minimal invasiveness. Several companies currently manufacture chemotherapy ports and more than 500,000 are annually implanted in the U.S.A. The prior art chemotherapy devices may be punctured by needles during access more than 1000 times by using a randomly spaced needle puncture technique, with small (i.e., typically 22 gauge) Huber point needles (i.e., so as to minimize coring of the septum). U.S. Pat. No. 4,569,675 depicts the first commercialized HD port.

Chemotherapy ports are not suitable for high rates of blood flow, since the blood flow passages cause abrupt changes in blood flow area, and such changes in flow area and/or flow direction are likely to cause damage to blood cells. The blood flow path also manifests "dead" flow zones and flow channeling which resist the flushing procedures used to eradicate contamination and/or hinders removal of previous drugs before instilling a new drug. Chemotherapy ports are also often subjected to long quiescent periods, and may suffer a loss of patency from blood entering, and clotting within, the port's blood path, thereby blocking blood flow. The Ensminger port patent, U.S. Pat. No. 5,057,084, which issued in 1991, teaches (1) an "enlarged funnel shaped" entrance to guide the transcutaneous tubular member (i.e., needle, fiber or catheter) to the port's flow passage, and (2) an "articulating catheter valve", rather than a septum, for preventing leakage of fluids from the port. The idea of the Ensminger patent is to provide a large target, thereby helping to guide the needle to enter the subcutaneous port's entrance, and to prevent damage to the conventional septum closure which may be caused by large needle punctures. Ensminger obtained an additional 12 patents issued as "continuations-in-part" of the initial patent, and all of these subsequent patents teach a port with a "funnel shaped" entrance and an "articulating infusion valve".

As will hereinafter be discussed, the present invention comprises neither a funnel-shaped entrance nor an "articulating" valve. It has been found that it is virtually impossible to pierce the epidermis and subcutaneous tissue and successfully enter a funnel-shaped entrance to a port aperture with the tip of a needle when using large diameter needles, such as those suitable for HD (see the Experimental Data section below). Ensminger correctly asserted that conventional septum/port designs may not be suitable for puncture by large needles. As will hereinafter be discussed, the present invention solves the problem by combining a novel septum/port configuration which, when used in conjunction with a novel subcutaneous tissue tract and lubrication, enables non-cutting needle penetration through subcutaneous tissue and port closure, without damage to the tissue tract or to the port closure.

Transcutaneous Port-Like HD Access Devices

Several companies introduced transcutaneous HD ports around 1985, including the Bentley Button® and Hemasite®. These devices were partially implanted, with a portion protruding externally from the surface of the skin The design of these prior art ports included a passage through the subcutaneous tissue, enabling a fluid circuit to be established between the central blood vessels of the patient and the HD machine without a transcutaneous puncture. However, such devices created a pathway for microbes to enter subcutaneous tissue along the interface between the tissue and the device. This was disastrous, with very high rates of infection and related patient deaths. All of the various versions of the product were subsequently abandoned.

Totally Implantable HD Ports

Biolink and Vasca were founded in the mid-1990s to develop totally implantable HD ports which were based on the notion that prior implanted ports demonstrated low infection and thrombosis as compared to catheters used for chemotherapy applications, and concluded that this experience could be replicated with HD ports. Both companies were not able to realize their expectations. Infection was an early problem, and thrombosis complications were only marginally better when compared with HD catheter infection rates. Unexpected problems occurred relating to large needle size, increased frequency of needle puncture and the necessary high blood flow rates, which imposed harsher conditions for hemodialysis access than those encountered during chemotherapy. Vasca and Biolink left the business by 2005 after considerable effort and expense.

Biolink Port

The inventors of the present invention were founders of Biolink, and contributed to Biolink's HD port development. Biolink's port product was called Dialock. Dialock was evaluated in a pilot clinical trial starting in 1996-infections occurred quickly. It was discovered that bloodstream infections could be treated by appropriate systemic antibiotics, and that simultaneous locking of the catheter with the same antibiotic avoided requiring removal of the port [Boorgu, R.; Dubrow, A. J.; Levin, N. W.; My, H.; Canaud, B. J.; Lentino, J. R.; Wentworth, D. W.; Hatch, D. A.; Megerman, J.; Prosl, F. R.; Gandhi, V. C.; Ing, T. S. Adjunctive Antibiotic/Anticoagulant Lock Therapy in the Treatment of Bacteremia Associated with the Use of a Subcutaneously Implanted Hemodialysis Access Device ASAIO Journal: November/December 2000—Volume 46—Issue 6—pp 767-770]. Although such treatment was effective as a salvage technique, the most critical objective was to avoid infection entirely.

Around 1996, Polaschegg and Sodemann learned of the antimicrobial drug Taurolidine, which did not induce bacterial resistance, making it attractive as an API for a long-term prophylaxis "lock". (Polaschegg H D. Taurolidine, a new antimicrobial catheter lock solution. Dialysis Times 2000; 7:1,8) Taurolidine and citrate were formulated into a lock solution by Dr. Sodemann (U.S. Pat. No. 6,166,007). Biolink developed a Taurolidine lock product which was accepted by European regulators. Results showed substantial improvement in reducing infections over a conventional HD catheter with heparin lock (Sodemann k, Polaschegg H-D, Feldmer B. Two Years Experience with Dialocks and CLS (A New Antimicrobial Lock Solution). BloodPurif. 2001:19:251-254). Furthermore, it was discovered that infections in tissue from needle punctures could be substantially reduced by injecting an antimicrobial "lock" into the tissue encapsulating the port, modifying the catheter lock instillation as follows:

(1) End HD session by stopping extracorporeal blood flowing to/from the port.

(2) Flush port/catheter internal flow lumen via the coupled port needle and return blood to the patient with ~10 mL sterile saline.

(3) Instill antimicrobial lock solution into each port lumen and catheter with a volume of antimicrobial "lock" solution approximating the internal volume of the port passage and the catheter lumen.

(4) Instill, or allow, the antimicrobial "lock" solution to be drawn into the port and the tissue tract during withdrawal of the needle from the port.

In the U.S., Dr. Allon, in separate trials, demonstrated a significant reduction in catheter-related bloodstream infections by using a Taurolidine "lock" instillation. (Allon M. Prophylaxis against Dialysis Catheter Related Bacteremia with a Novel Antimicrobial Lock Solution. Clinical Infectious Diseases 2003; 36; 1539-44). However, serious tissue healing complications, caused by frequent puncturing with large needles, and the difficulty of establishing blood access by many nurses, remained a problem. These deficiencies in Dialock performance would ultimately limit adoption of port accessing and Biolink declared bankruptcy around 2004.

Vasca Port

Vasca's port, called "Lifesite", was a novel port design. The device and the ancillary devices and compositions are described in several patents (Burbank J H, Brugger J M, Heslin J M. 2001. Valve port and method for vascular access, PCT Patent WO01/32141, Finch C D, Burbank J H, Brugger J M. 2000. Method and apparatus for percutaneously accessing an implanted port, U.S. Pat. No. 6,120,492, Burbank J H, Finch C D, Brugger J M, Kuiper H E. 1999. Valve port and method for vascular access, U.S. Pat. No. 6,007,516; Finch C D, Burbank J H, Brugger J M. 1999. Method and apparatus for percutaneously accessing an implanted port; U.S. Pat. No. 5,989,239, Utterberg D S, Swindler F G, Ellis G. 2003. High viscosity antibacterials for cannulae; US Patent 20030175323, Utterberg D S, Swindler F G, Ellis G. 2003. High viscosity antibacterials for cannulae; US Patent 20030175323] describing an apparatus and method of use).

Vasca obtained U.S. approval for commercial distribution of Lifesiteand sold the product for approximately 4 years (i.e., between approximately 2000 and 2005). The company closed operations by 2006 after several failures and FDA safety warnings. Lifesite was found to induce many complications in patients, including surgical site infections and needle puncture site infections, which were aggravated by poor tissue healing around the needle puncture site. Use of the BH ("buttonhole", see below) needle guidance technique in conjunction with Lifesite was a factor in several infection episodes, in spite of various prophylactic measures (John J. Ross, Geetha Narayan, Ellen K. Bergeron, Michael G. Worthington, and James A. Strom. Infections Associated with Use of the LifeSite Hemodialysis Access System. Clinical Infectious Diseases 2002; 35:93-5.). Misalignment of the BH-type needle tract with the port's entrance resulted in failures to access correctly. Several factors may have contributed to poor performance:

(1) large needle size (i.e., 14 gauge) and poor closure of the needle tract after needle withdrawal;

(2) poor subcutaneous tissue healing and infection of the tissue around the needle tract;

(3) short length of the needle tract in subcutaneous tissue, with the perpendicular, protruding needle exiting from patient's skin, susceptible to inadvertent bumping and/or tearing of tissue and dislodgement;

(4) the size and orientation of the implanted Lifesite created high tensile stress in the tissue acting on the BH tract, which tended to open the BH tract;

(5) sealing/locking of the docked needle within the port was not reliable, and could be compromised by forces acting on the protruding needle, resulting in blood leakage during the HD treatment;

(6) in vivo shifting of the port relative to the BH tract caused misalignment of the port relative to the BH, so that needles were guided away from the port entrance, creating difficulty in accessing the blood and/or causing missed dialysis sessions;

(7) antimicrobial prophylaxis was not "locked" within the luminal passages of the port during the quiescent period, so biofilm (or microbes) entering the catheter would not be exposed to a biocide; and (8) the Lifesite design was subject to "single fault" failure caused by needle dislodgement.

Gel Catheter Locks

Vasca and Medisystems filed several patents claiming antimicrobial protection, including gel compositions. Two Utterberg patents claim a gel lock, but they fail to teach the comprehensive rheology characteristics necessary to achieve the required function and safety for a gel catheter lock. "Many non-newtonian fluids not only exhibit viscosity which depends on shear rate, (pseudoplastic or dilatant) but also exhibit elastic properties. These visco-elastic fluids require a large number of strain rate material properties in addition to shear viscosity to characterize them. The situation can be complex when the material properties are time dependent (thixotropic or rheopectic)" (McGraw-Hill Encyclopedia: Science & Technology (2002) Vol 19 p. 304).

Important rheology characteristics are required for effective gel prophylaxis when used as a port/catheter "lock" and need to encompass an array of properties, including but not limited to:

I. Visco-elastic gel matrix with several rheological properties:
  a. syringeable to enable instillation and withdrawal to/from port;
  b. yield shear strength enabling maintenance of the gel within the catheter and needle tract under mechanical shock loading, and pressures low enough to be overcome with a syringe (i.e., achieving flowability);
  c. "die swell" characteristics to fully fill catheter lumens and other spaces;
  d. plug flow profile rather than a laminar flow profile, as in water solutions, to avoid spillage;
  e. tensile strength sufficient to maintain cohesive structure of gel during withdrawal from, or inadvertent injection into, a patient;
  f. low viscosity, permitting an acceptable withdrawal time from a catheter;
  g. preferable shear thinning behavior; and
  h. capability to return to solid-like properties upon return to a zero-strain rate.

II. Visco-elastic material must be biocompatible.

III. Gel must be dissolvable so as to not permanently block blood flow in the small vessels.

Arterio-Venous Fistulas

The arterio-venous fistula (AVF) is asserted (by most nephrology and vascular surgery literature) to be the most reliable means of blood access. AVF is currently used by most HD patients. AVF is constructed by joining a large artery and large vein, usually in the arm. This surgical construct subjects the vein to increased pulsating pressure, thereby inducing growth in the vessel diameter and wall thickness, and increasing the strength of the blood vessel. Under appropriate conditions, the AVF construct may transform into a suitable subcutaneous access, capable of sustaining repeated puncture by dialysis needles, and may thereby enable the withdrawal of blood, at sufficiently high flow rate so as to be suitable for effective HD. Accordingly, AVF is constructed to produce an approximate order of magnitude higher blood flow in an arm than was to be found in the arm before AVF construction. Extreme anomalous flow conditions cause vascular and heart deformities, which are related to high complications and mortality. Nevertheless, AVF is the standard of care for most patients, since AVF does not suffer from the poor long-term infection complications of non-protected catheters.

Several weeks or months after construction, AVF may mature to usability as an HD access. In the U.S., approximately 40% of AVF constructions never function effectively. Many functioning AVF patients are subject to extremely high cardiac blood flow, which increases their risk of death from cardio-venous events. (Peterson W J, Barker J, Allon M. Disparities in fistula maturation persists despite preoperative vascular mapping. Clin J Am Soc Nephrol 2008; 3:437-41; Weber C L, Djurdjev O, Levin A, Kiaii M. Outcomes of vascular access creation prior to dialysis: building the case for early referral. ASAIO J 2009; 55:355-60; Maya ID, O'Neal J C, Young C J, Barker-Finkel J, Allon M. Outcomes of brachiocephalic fistulas, transposed brachiobasilic fistulas, and upper arm grafts. Clin J Am Soc Nephrol 2009; 4:86-92; Huijbregts H J, Bots M L, Wittens C H, Schrama Y C, Moll F L, Blankestijn P J; CIMINO study group. Hemodialysis arteriovenous fistula patency revisited: results of a prospective, multicenter initiative. Clin J Am Soc Nephrol 2008; 3:714-9; Field M, MacNamara K, Bailey G, Jaipersad A, Morgan R H, Pherwani A D. Primary patency rates of AV fistulas and the effect of patient variables. J Vasc Access 2008; 9:45-50).

AVF superiority is somewhat misconstrued as many patients are not considered appropriate for AVF placement, and many patients who receive an AVF surgical construct do not achieve useful outcomes. For a long time, the only reported outcome data for AVF was instances in which AVF had been operating for some period of time, so that those instances in which AVF never operated were not accounted for in the reported data. (Ridao-Cano N, Polo J R, Polo J, Perez-Garcia R, Sanchez M, Gomez-Campdera F J. Vascular access for dialysis in the elderly. Blood Purif 2002; 20:563-8; Hodges T C, Fillinger M F, Zwolak R M, Walsh D B, Bech F, Cronenwett J L. Longitudinal comparison of dialysis access methods: risk factors for failure. J Vasc Surg. 1997 December; 26(6):1009-19).

Recent data suggest that the failure of an AVF to mature is related to fundamental vascular properties, rather than to poor surgical technique, which was thought to be improvable with training (Kheda M F, Brenner L E, Patel M J, Wynn J J, White J J, Prisant L M, Jones S A, Paulson W D. Influence of arterial elasticity and vessel dilatation on arteriovenous fistula maturation: a prospective cohort study. Nephrol Dial Transplant 2010; 25:525-31).

The high flow necessary for proper functioning of the AVF access is created by joining a midsize or large artery to a midsize, or large, vein, thereby shunting blood flow away from the capillary bed (i.e., short-circuiting the capillary bed) and resulting in a substantially higher (i.e., an order of magnitude increase) blood flow rate in the shunt than what is physiologically natural. The increased blood flow rate is accompanied by a substantial anomalous blood flow increase through the heart.

AVF and AVG (Arterio-Venous Graft, see below) associated pulmonary hypertension has been found to correlate with access flow (Yu T M, Cheng C H, Shu K H). Influence of Access Blood Flow on Pulmonary Hypertension in Patients Undergoing Hemodialysis. J Am Soc Nephrol 2008; 19:261 A; Abdelwhab S, Elshinnawy S. Pulmonary hypertension in chronic renal failure patients. Am J Nephrol 2008; 28:990-7; Nakhoul F, Yigla M, Gilman R, Reisner S A, Abassi Z. The pathogenesis of pulmonary hypertension in haemodialysis patients via arterio-venous access. Nephrol Dial Transplant 2005; 20:1686-92)

Clinical studies reveal that high cardiac blood flow produces anomalous structural changes in the heart, which correlate with high mortality. (Iwashima Y, Horio T, Takami Y, Inenaga T, Nishikimi T, Takishita S, Kawano Y. Effects of the creation of arteriovenous fistula for hemodialysis on cardiac function and natriuretic peptide levels in CRF. Am J Kidney Dis 2002; 40:974-82, Savage M T, Ferro C J, Sassano A, Tomson C R. The impact of AVF formation on central hemodynamic pressures in chronic renal failure patients: A prospective study. Am J Kidney Dis 2002; 40:753-9, On Y, Korzets A, Katz M, Erman A, Weinstein T, Malachi T, Gafter U. The contribution of an arteriovenous access for hemodialysis to left ventricular hypertrophy. Am J Kidney Dis 2002; 40:745-52, Bos W J, Zietse R, Wesseling K H, Westerhof N. Effects of arteriovenous fistulas on cardiac oxygen supply and demand. Kidney Int 1999; 55:2049-53,).

Catheter and port accesses do not produce short circuit pathways, do not increase blood flow through the heart and do not deform the heart. AVF has intrinsic operational failure modes which are more likely to occur in patient-performed HD treatment in the home including, but not limited to, (a) needle dislodgement, (b) needle insertion mistakes and complications, (c) connection integrity during HD treatment, (d) needle withdrawal with associated long bleeding episodes (i.e., failure to form a clot capable of stopping bleeding) and (e) physical damage to access during the quiescent period between HD sessions. Risks to the patient include major blood loss during HD, long bleeding times after needle withdrawal, damage from improper coupling (including tearing of the AVF construct), infection of subcutaneous tissue and of the needle tract, blood flow blockage/loss of flow, extravagation of returned blood, and physical damage to the AVF, which is vulnerable to mechanical injury. "Bleed out", and death from a break in the return blood flow path, is especially feared by patients during HD. Needle dislodgement from the AVF in the return line may produce a high velocity "jet spray" of blood into the room. Within a few minutes, patient blood pressure will drop precipitously, and the patient will die without rapid medical intervention. Current HD machines account, indirectly, for this situation by sensing a pressure drop in the blood lines, however, this is not a reliable indication of needle pull-out. Much of the resistance formed in the flow circuitry (i.e., accounting for the sensed pressure in the blood lines) with AVF access is formed by the needle, and as long as the blood flow rate stays high, needle resistance will not change appreciably. Only when the patient's blood volume drops precipitously will the pressure drop indicate that there is a problem.

Another method used to sense needle dislodgement is the use of blood detectors, which can be arranged around the body of the patient. Again however, this is not a reliable indicator of a needle pull-out, since high velocity jet spray may avoid the area near a detector and thereby avoid detection. Needle pull-out with severe consequences even occurs in HD clinics with nurses and other patients nearby (Hurst J. A Costly Complication: Venous Needle Dislodgement Sep. 27, 2010). http://www.renalbusiness.com/articles/2010/09/venous-needle-dislodgement.aspx Obviously, a solitary patient receiving nocturnal dialysis at home is at an even greater risk for "single fault" failure of needle pull-out. "Single fault" failure is the term used to indicate failure resulting from a single event, which may cause the entire system to fail (i.e., which may cause patient death). Design review procedures are used to identify "single point" failures and "re-design them out", if possible. European Medical Device Regulations require a formal Reliability Analysis for device approval, and any design which permits a "single point" failure would not be approved. AVF and AVG have inherent "Single Point" failure modes which are not easily overcome. (Polaschegg HD. Venous needle dislodgement: the pitfalls of venous pressure measurement and possible alternatives, a review. J Ren Care 2010; 36:41-8)

Patients report aversions to AVF, including trypanophobia, difficulty self-accessing, poor self body image, frequent bleeding occurrences, fragility and a sense of danger from access failure, and loss of arm function. AVF also requires a significant investment long before it is useable. Patients are screened to determine suitability for AVF. Most new HD patients receive both a catheter and an AVF prior to starting HD because the AVF is not already working in the patient. Upon verifiable confidence of AVF functionality, after several HD sessions, the catheter is removed.

Usually, each HD clinic has specially trained puncture nurses to perform AVF accessing along the steps outlined below:

(1) Set up a sterile field for performing the AVF access.

(2) Examine the AVF for any signs of damage and/or infection, and evaluate previous needle puncture sites for any evidence of poor healing. Nurses may use a stethoscope to monitor the AVF along its length.

(3) Select the needle puncture target, locating the target at some distance away from the previous puncture sites used over the previous few weeks. This permits tissue healing of the puncture area before a new puncture is attempted. Locating a needle puncture target may include touching and feeling the AVF to get a sense of resiliency along the length of the AVF.

(4) Topically clean and sterilize the area of skin over the AVF in the vicinity of the puncture site.

(5) Using a thumb and forefinger, straddle the AVF site to hold and stabilize the AVF.

(6) Hold the needle with the other hand and position the tip of the needle so as to face toward the artery side of the AVF, and so that the tip bevel faces appropriately, and puncture the tissue at a 30° angle with the plane of the fistula, along the longitudinal axis. Push the needle through the subcutaneous tissue, seeking to position the tip of the needle near the center of the circular cross-section of the AVF. It is critically important that the tip of the needle be within the AVF, and not puncture the far side of the wall of the AVF. Position the tip wholly within the AVF. Secure the needle to the patient with tape.

(7) Insert a second needle in a similar fashion, except that the tip of the second needle should face the opposite direction of the tip of the first needle, and should be separated from the first needle by a distance so as to minimize the occurrence of blood being withdrawn by the first line directly from the return line (i.e., to minimize drawing blood exiting from the second needle into the first needle, which can compromise treatment efficacy). Secure the second needle to the patient.

(8) Position the bloodlines and tape the bloodlines to the arm of the patient.

(9) Initiate dialysis. Examine the external circuit for blood leaks, and check the blood line pressures, etc., for proper HD processing. (van Loon M M, Kessels A G, van der Sande F M, Tordoir J H. Cannulation practice patterns in haemodialysis vascular access: predictors for unsuccessful cannulation. J Ren Care 2009; 35:82-9; Van Waeleghem J P, Ysebaert D. Vascular access in haemodialysis. Part 2. EDTNA-ERCA Journal 1995; 21:RCD9-14; Brouwer D J. Cannulation Camp: Basic Needle Cannulation Training for Dialysis Staff. Dialysis & Transplantation 1995; 24:606-12).

Puncturing (i.e., accessing) the AVF with a needle suitable for HD is considerably more difficult for a patient having only a single free hand. The location of AVF on the upper arm is especially awkward for the patient when accessing the AVF with a needle. With poor visualization, accessing the AVF and stabilizing the AVF without the benefit of a second hand increases the likelihood of an inaccurate needle puncture into the AVF. Judging the correct depth for needle penetration without tactile or visual clues is also difficult. Taping needles in place with one hand is neither easy nor is it done in a particularly robust fashion (considering its criticality). Many people suffer trypanophobia, making it difficult for them to stick themselves with needles since they anticipate pain from the needle stick.

Removing needles from an AVF is an especially high-risk procedure without the benefit of a second free hand. Nurses typically use one hand to press down on the skin/tissue over the needle tract to stop bleeding from the needle tract, while extracting the needle from the access point with the other hand. Force is applied to the tissue above the needle track continuously for several minutes so as to allow clot formation within the puncture tract or within the conventional BH tract. The clot which is formed must be capable of withstanding an internal pulsating pressure within the AVF (i.e., the blood pressure inside the AVF is approximately 5 to 40 mmHg (or more) than venous blood, and HD patients are commonly heparinized during HD treatment). Experience demonstrates that if blood is permitted to flow out of the patient after needle withdrawal, the total time to stop bleeding will be substantially longer than if blood flow out of the patient never occurred. Patients report long bleeding time episodes on a frequent basis when self-accessing the AVF.

Patients are warned not to use their AVF arm for strenuous activities, not to engage in physical activities and not to put pressure on the AVF, e.g., by resting one's head on the AVF. Patients with AVF access suffer a sense of vulnerability. In a recent survey, patients with AVF report that AVF access evokes a sense of stigma and poor body image. (Richard, C. J., & Engebretson, J. Negotiating living with an arteriovenous fistula for hemodialysis. Nephrology Nursing Journal, 37(4), 363-375-2010).

Chemotherapy patients in the 1980s sensed poor self-image when using external catheters. Patients often requested ports after observing other patients using ports in the chemotherapy clinic. Patient preference has helped to bring about rapid adoption of ports for cancer chemotherapy.

Catheters are used as primary blood access in about 80% of new US HD patients in spite of the nearly universal low regard which such access is held in by much of the medical community. (Goldstein S L, Ikizler T A, Zappitelli M, Silverstein D M, Ayus J C. Non-infected hemodialysis catheters are associated with increased inflammation compared to AVF. Kidney Int. 2009 November; 76(10):1063-9. Epub 2009 Aug. 12.) Catheters are extremely important to enable initiation of HD, since catheters are immediately functional, provide access to the blood immediately after placement, are suitable for virtually all patients, and because placement of a catheter is fast and requires less specialized surgical skill. The dominant criticism of catheters is directed at their high catheter-associated bacteremia. Studies show that catheter-associated bacteremia may be substantially reduced by the use of an antimicrobial "lock" solution. Antimicrobial "lock" solutions are not yet available in the U.S., although such solutions would significantly reduce hospitalization (and other infection complications) on the incident patients who now rely on catheters for their HD.

Arterio-Venous Graft (AVG)

AVG was previously the most commonly used HD access in the U.S. until around 2005, when it was displaced by AVF, which was considered to be less prone to complications. AVG uses a tube made of synthetic material, such as expanded Teflon, approximately 5-8 mm in diameter and 5 to 10 inches in length. This conduit is surgically implanted in the patient so as to shunt blood from an artery to a vein in a manner similar to that of the AVF. The conduit material is typically porous, allowing tissue ingrowth into the open structure. The method of accessing the AVG is done in a similar fashion to accessing of the AVF, using special HD puncturing needles. The same complications found in the use of AVF are also found in the AVG, including difficulty in performing self-accessing by the patient. The maturation time required for the AVG is shorter than the maturation time required for the AVF.

Permanent Hemodialysis Catheter (PHDC)

Permanent Hemodialysis Catheter (PHDC) is used mainly in newly treated ESRD hemodialysis patients in the U.S. (i.e., for approximately 80% of patients starting HD). The prevalence rate of catheter use in the U.S. is about 25% of the total HD population. PHDC is considered by the nephrology community to be the least reliable blood access means, due to of higher rates of blood stream infections per days of use when compared to AVF or AVG. Catheters are removed when, and if, the patient's AVF or AVG matures. Other complications of PHDC are thrombosis and an inability to achieve the highest blood flow rates favored by clinics (which enables the shortest HD time based on Kt/V criteria). Infection rates of catheters are substantially lower when using antimicrobial catheter "locks" but such catheter "locks" are not yet available in the U.S.

Button-Hole Needling Technique with Arterio-Venous Fistulas

The Button-hole ("BH") needle technique, combined with AVF access, began to be used around the middle of 1990 as an alternative to using spaced punctures through the subcutaneous tissue by sharp HD needles. (Twardowski Z J. Nat Clin Pract Nephrol 2007; 3:648-9). The BH is created after the AVF demonstrates functionality using the spaced puncture technique, and the BH is not employed until confidence develops that the AVF is functioning properly. The BH tract is created by a specialist at the clinic. The specialist selects the optimum location and alignment for the BH. Preparing for a HD session, the specialist will make the needle puncture for the HD treatment. At subsequent sessions, the specialist will attempt to access AVF by repeated needle puncture along the same puncture line previously made. This technique will be followed for a few weeks. It has been found that repeated needle puncturing through the same subcutaneous wound, carried out regularly over a period of about 3 weeks, creates a build-up of hard tissue which is useable as a pathway (or "buttonhole) for needle penetration. Putative etiology is that repeated tissue injury by the cutting and healing of the subcutaneous tissue along the same "line" forms "scar tissue". This formation of scar tissue creates a "line" which can often be penetrated by a dulled HD needle. It is reported that this tract (i.e., "line") enables subcutaneous penetration with less pain to the patient, and less bleeding from the patient, than that experienced by the previous spaced puncturing of AVF with sharp needles. Accordingly, in the absence of other attractive options, BH is becoming a favored access choice for home HD. However, the BH technique still requires blood to enter the needle tract upon withdrawal of the needle, and formation of a clot within the needle tract, so as to seal off the needle tract and prevent bleeding. Additionally, it is necessary that the clot be removed from the tract before inserting a needle for a subsequent HD session.

The BH should be maintained with strict cleanliness, dryness and bandaging to affect BH closure and to prevent microbe colonization. Many home HD patients are using the BH tract in conjunction with AVF, since the BH tract helps guide the needle, and has been associated with less bleeding (although this has not been subjected to randomized studies). With increased use of BH/AVF accessing, studies report higher rates of bacteremia and access site infections with BH/AVF than when using the AVF and variable puncture site accessing procedure (Kant K S, Duncan H J, Tallarico B J, McKinney R A. Does the Buttonhole Technique of AV Fistula Cannulation Increase Risk of Bacteremia?. J Am Soc Nephrol 2008; 19:262 A, Carolyn L. Van EPS, Mark JONES, Tsun N G, David W. JOHNSON, Scott B. CAMPBELL, Nicole M. ISBEL, David W. MUDGE, Elaine BELLER, Carmel M. HAWLEY. The impact of extended-hours home hemodialysis and buttonhole cannulation technique on hospitalization rates for septic events related to dialysis access. Hemodialysis International. Volume 14, Issue 4, pages 451-463, October 2010). Higher rates of infections with BH are to be expected, since the "scar tissue" tract through the subcutaneous tissue does not close securely (compared to the closure of healed subcutaneous tissue). Furthermore, the intrinsic blood clots formed within the BH tract may become integrated with microbes and may provide a sanctuary for microbes outside of the host's natural (i.e., immune) defense response. Fragments of an infected blood clot may enter a patient's bloodstream during subsequent penetration by a needle and may cause bloodstream infection. Furthermore, BH passageways often exhibit tissue growth infiltration, which may result in blocking the entry of a non-cutting needle. Such blocking necessitates piercing with a cutting tool to open the BH tract. Creation of a BH passageway to the AVF is usually performed by a puncture specialist in the clinic. The specialist selects an entry point on the skin and seeks to produce a straight line puncture to the center of the AVF, at an angle of entry to the skin surface which provides a suitable length for the subcutaneous tract. The act of needle puncture is performed blind, without tools guiding the line of the puncture tract from its starting point on the skin. After the initial piercing procedure, repeated piercings with a standard HD needle are performed, preferably by the same specialist, attempting to replicate the same piercing line as performed initially. In 2-3 weeks, a robust scar tissue forms within the subcutaneous tissue along the needle puncture tract, enabling a relatively non-sharp needle to subsequently penetrate the scar tissue formation, with less bleeding and with less pain to the patient. If, indeed, the BH tract performs as required, patient training may begin for self-accessing. In a few more weeks the patient may solo self-access.

Vasca's instructions recommended the BH technique for needle docking with a Lifesite port. Frequent complications occurred with their Lifesite port/BH technique:

(1) The BH and the surrounding subcutaneous tissue experienced significant infection in spite of considerable attention to aseptic procedures, and in spite of the use of a prophylaxis instillation within the BH tract.

(2) The BH remained open in some patients, exposing the tract and the Lifesite to contamination and infection risk.

(3) Nurses experienced difficulty in making the connection of the needle to the port via the BH tract. It was determined that the Lifesite port shifted within the encapsulating tissue surrounding the port, thereby resulting in misalignment of the BH tract with the entrance to the port.

(4) Some patients experienced bleeding from the port during HD treatment.

Preparation for HD using a BH requires topical aseptic cleaning around the needle entry point on the skin, and removal of the clot, before insertion of a needle for an HD treatment. Considering that the clot may be infected, it is important to remove the clot rather than push the clot into the patient. Often it is difficult to determine if the clot is entirely removed.

OBJECTIVES OF THE PRESENT INVENTION

The present invention comprises an advanced system for HD blood accessing which substantially improves the human interface, enables most patients to perform self-access as required by HD therapy, and which patients find useful, safe and non-disfiguring. The system comprises:

(1) Improved performance, safety and ease of use, enabling patient self-accessing, provides greater control of their treatment and offers substantially improved outcomes when compared to clinic-based treatment.

(2) No "single fault" failure mode from needle dislodgement.

(3) Needle coupling that is precisely guided to the implanted port and to the docking position, with automatic opening of the blood path and positive confirmation of the docking position.

(4) Redundant lock features to prevent needles from disengaging from the implanted port.

(5) Easy withdrawal of needles from the body of the patient, with automatic closure of the blood pathway.

(6) No bleeding through all stages of access, use and during the quiescent period between treatments (i.e., eliminates the severe bleeding that often occurs with needle withdrawal from AVF/AVG).

(7) Effective prophylaxis against infection for the HD access blood path, needle guidance tract and the tissue capsule around port.

(8) Gel lubricant and prophylaxis enabling easy penetration with a blunt needle (or trocar) and passage through the tissue tract and through the port closure mechanism without bleeding, and with minimal wear or damage over a long life.

(9) Gel composition rheology characteristics enabling no spillage of the catheter lock and redundant sealing against blood leaks and/or against air infiltration during the quiescent period in the event of a primary failure.

(10) Non-cutting needle which is enabled to cross tissue and port valving so as to establish a transcutaneous flow path which does not damage tissue or the septum closure mechanism.

(11) System which enables effective HD without increasing blood flow through the heart, unlike with an AVF or AVG access.

(12) Low costs for apparatus (ancillary needles and bloodline) and surgical placement, unlike with an AVF or AVG.

(13) Gel "lock" which blocks blood from entering the port/catheter during long periods of residence time, and which provides prophylaxis against infection for internal passages and the surrounding subcutaneous tissue.

(14) Improved design for a chemotherapy port, with improved flow passage design for better rinseability, allowing safer switching of drugs and enabling long quiescent periods without the risk of blood exchange with the lock, which results in clotting and lost patency.

(15) Hydrophobic gel for instillation into a tissue tract or BH, which does not wash away in aqueous solutions.

(16) Port placement which patients perceive as better for self-image, and not a cause for stigmatization, as is commonly found with AVF.

(17) Tissue tract morphology which is tailored to improve upon the functionality of needle coupling to the port, by providing for precise guidance through the subcutaneous tissue, and a means to maintain alignment of the needle with a port.

(18) Tissue tract prophylactic lubricant compositions which improve prophylaxis and the ease of needle entry.

(19) Tools and methods to construct a novel tissue tract.

(20) Advanced external blood circuit apparatus integrating needles, bloodline and dialyzer into a single seamless assembly which has a smooth, gently changing flow area, with no "dead" volumes or spaces producing flow perturbations. The apparatus is capable of multiple use and sterilization enabling several uses rather than single use.

(21) Small home sterilizer which is programmable to clean and sterilize the advanced external blood circuit assembly.

SUMMARY OF THE INVENTION

The present invention enables safer and easier patient self-accessing for HD treatment outside a HD clinic. The present invention encompasses several novel aspects, including a very simple HD port which connects to a fully-blunted, non-cutting needle, and which is guided to cross subcutaneous tissue and precisely enter the port along a novel bio-engineered tissue tract. Insertion of a needle via the tissue tract entering the port aperture automatically opens a blood pathway, and the needle reaches a positive tactile stop corresponding to the correct docking position. Two needles establishing the blood path interface are attachable to one another, thereby eliminating "single fault" failure from needle dislodgement and enabling a redundant locking of the needles to the implanted port, preventing needle disengagement from the port. Novel tools and methods of use facilitate creation of the tissue tract in a precise and permanent alignment with port apertures so as to provide for accurate, repeated needle insertions. The present invention also includes an ancillary lubricant/prophylactic gel which facilitates needle insertion and provides long life of the septum and of the tissue tract, and which also provides prophylaxis against biofilm formation along the blood lumens of the port and the needle passage, which are common targets for infection. A redundant sealing effect may be achieved by use of a special visco-elastic gel lock formulation which prevents bleeding, even in the event of primary port valving failure. An ancillary needle/bloodline connection improves reliability over current apparatus. An alternate, external blood circuit is described which improves usability with the permanent factory-assembled external blood circuit comprising needles, bloodline and dialyzer. This eliminates several connections otherwise made by the patient, which reduces the risk of disengagement causing bleedout. The system is substantially more robust than other accessing methods. Several improvements are especially "patient friendly". By enabling self-accessing capability, which is easy and safe without any bleeding or pain, patients maintain better self-image compared to prior art blood access systems, which most patients find repugnant. The present invention is helpful in attracting patients to adopt home dialysis so as to achieve a better quality of life, self-reliance and control of their lives. Large scale adoption of home dialysis will bring substantial cost savings in ESRD treatment which is considered non-sustainable on its present course.

In one preferred form of the invention, there is provided a medical blood access system used for hemodialysis treatment to enable blood withdrawal for processing of blood by an external apparatus and return the same blood to a patient, comprising an interfacial fluid conduit between the machine and patient's blood supply which is repeatedly connectable along a guided pathway passing through epidermis and subcutaneous tissue via a naturally formed tissue tract to enter blood space, providing improved patient safely, convenience, effective prophylaxis, without bleeding or tissue trauma or pain, and is executable by the patient to precisely connect and disconnect with minimal disfigurement or life restrictions, and is useable on virtually all patients soon after placement and is robust and safe to high blood flow.

In another preferred form of the invention, there is provided tools for initiating tissue tract formation to facilitate best alignment and fixation with a port aperture during surgical port placement, comprising:

a piercing tool which is used in conjunction with the port to establish precise alignment; and a "foreign body" tool which provides surface and establishes position within subcutaneous tissue to effect a tissue tract formation conjoined with the membrane capsule forming around the port under full visual access and allowing port position adjustment if necessary while the patient is somewhat less alert and to enable a contiguous conjoined membrane encapsulation with the port.

In another preferred form of the invention, there is provided a method for surgically inducing tissue tract formation, comprising:

a. determining patient preferences for accessing and vascular conditions;

b. inserting a catheter using the Seldinger technique using usual practice and establish the correct position of the catheter tip in the right atrium using an imaging technique;

c. testing flow patency during instillation and withdrawal of fluid, and fixing the catheter near the insertion site of vessel;

d. creating a pocket for the port, and verifying size;

e. creating a tunnel from the insertion site of the catheter to the pocket;

f. inserting a piercing tool, retrograde, through the integral port tubes which are the catheter attachment points and pushing the piercing tool so as to enter the port passage and penetrate the port's septum but not exit the other end of the port passage;

g. positioning the port in the pocket and suturing the port to the underlying fascia using the suture sites integral with the port housing;

h. positioning skin and subcutaneous tissue which is wide open into a position it will take after pocket closure and restrain the skin and subcutaneous tissue with temporary means;

i. continuing insertion of the piercing tool such that it exits the port and advances through the subcutaneous tissue in a line projected from the port's entrance aperture and penetrates the epidermis and protrudes from the skin;

j. removing the piercing tool and inserting the "foreign body" platform tool along the pierced path just created and passing the probe end of the tool into the port's aperture as completely allowed;

k. positioning the wings of the tool such that the flat surface is in the orientation, with minimal tensile stress, in the local subcutaneous tissue (i.e., in position to minimize the opening tendency of the tract);

l. cutting the catheter to correct length and attaching the catheter to the port body;

m. fixing the tool temporarily in this position outside the body;

n. closing the pocket;

o. removing the "foreign body" tool and flushing the port/catheter with antimicrobial lock solution;

p. replacing the "foreign body" tool and fixing it in place and applying an antimicrobial dressing; and q. maintaining in a clean condition for approximately 1 week to allow for the tissue tract formation if hemodialysis is required sooner, repeat steps o. and n. to allow for needle coupling with the port to provide access for hemodialysis treatment and subsequently reinsert the tool to enable fuller tract formation.

In another preferred form of the invention, there is provided a subcutaneous hemodialysis port comprising a septum comprising an opening, the septum being held in the port under compression so as to normally close off the opening.

In another preferred form of the invention, there is provided a subcutaneous hemodialysis port comprising a tissue anchor formed around an opening in the port, the tissue anchor comprising means for anchoring one end of a tissue tract to the port so that the tissue tract is aligned with the opening.

In another preferred form of the invention, there is provided a subcutaneous hemodialysis port comprising means for releasably locking a hemodialysis needle to the port.

In another preferred form of the invention, there is provided a construct comprising a port implanted in a body beneath the surface of the skin, the port being connected to the interior of a vascular structure by a catheter and the port being connected to the surface of the skin by a tissue tract, with a septum being interposed between the catheter and the tissue tract, wherein the septum is selectively penetrable.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
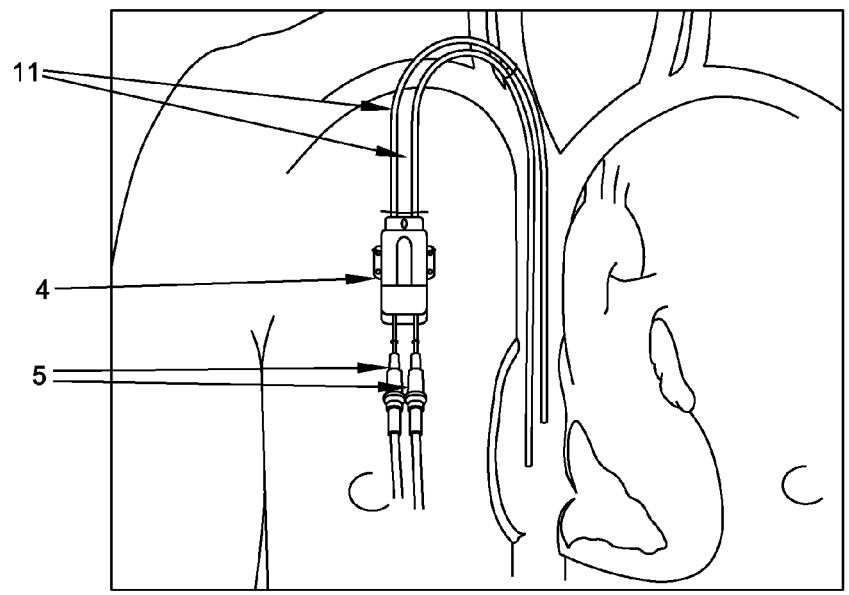
FIG. 1 is a schematic view showing a hemodialysis port installed in a patient.

The present invention is a system comprising apparatus, compositions, and methods of use for improving performance, safety and ease of performing blood access by patients without assistance from another person.

The apparatus elements of the invention are a port with interfacial features which enable a bio-engineered tissue tract attachment; a blunt needle assembly; a factory-assembled external blood circuit; and tools to create a tissue tract. A composition comprising a gel lubricant having antimicrobial action enables large needle penetration of, and passage through, tissue. The invention also comprises methods for tissue tract formation with precise alignment to the port, and means to maintain alignment over a long period of time. Other novel methods of use include user (e.g., the patient) instillation of gels during needle withdrawal.

The gel composition protects the catheter and the tissue tract against biofilm formation, and the inherent lubrication qualities of the gel help reduce wear and damage to the port closure (i.e., the septum) and to the tissue tract.

The novel approach for tissue tract creation includes tools which enable simple creation, and accurate needle guidance, so as to a correct docking position within the port. The tissue tract forms as a single contiguous tissue membrane in conjunction with contemporaneous port encapsulation. Precise alignment of the needle tract (i.e., the tissue tract) enables easy, guided patient accessing. Tissue tract alignment is fixed, and will not shift, thereby avoiding a misdirected needle insertion away from the targeted port aperture. Contiguous encapsulation enables the use of a single prophylaxis source for both the port and tissue tract.

Accessing is completely bloodless, since cutting or piercing of tissue during needle puncture is eliminated, and allows for the instant closure of the septum upon withdrawal of the needle, which eliminates bleeding and clot formation as in prior BH/AVF accessing.

The system improves safety and reliability over the full HD operational cycle. The common problem of "single fault" failure from needle dislodgement during HD has been designed out. The port, the needle and the bloodline connections incorporate "fail safe" techniques and/or redundancy design for improved reliability. More reliable sealing is provided by the sealing of the septum around the needle during HD, as compared to previous HD port designs.

Patients treated in HD clinics should be more inclined to dialyze at home once they are aware of easier and safer self-accessing. (Home Hemodialysis Fact Sheet, American Nephrology Nurse's Association 2007 www.annanurse.org)

Many patients feeling stigmatized by their current access should understand that a small, totally implanted device provides better self-image, better security and greater freedom than access associated with an AVF or a catheter.

The accessing system adds many advantages to the healthcare system by attracting patients to home HD:

(1) Implantation of a port and a tissue tract is suitable for virtually all patients and the port and tissue tract function immediately in virtually all patients who receive the port and tissue tract. Accordingly, the need to create two redundant access systems per patient (i.e., AVF and catheters) can be eliminated.

(2) Approximately 90% of bloodstream infections and tissue infections may be eliminated by using gel "lock" prophylaxis.

(3) A potential reduction in mortality rates, since AVF patients suffer from cardio-vascular complications which are related to AVF's inherent high rate of cardiac blood flow, and therefore suffer from higher mortality rates.

(4) A cost savings which may result from patient-performed HD in the patient's own home, rather than HD performed in private HD clinics.

(5) A cost savings from a reduced use of drugs and hospitalizations, which has been demonstrated by home dialysis studies.

(6) Patient rehabilitation and return to the work force.

Looking now at FIG. 1, there is shown a diagrammatic view of a dual passage port device 4 illustrative of an embodiment of the present invention, implanted in subcutaneous tissue. Two needles 5 are shown inserted through the subcutaneous tissue so as to couple with port 4. Port 4 comprises an internal septum 6 (not shown in FIG. 1) and a catheter 11 for each passage. Port 4 is placed subcutaneously by a surgeon, with its catheters 11 inserted into a large blood vessel. Typically, catheters are inserted into the internal jugular vein, with the distal tips of catheters 11 residing in the right atrium of the heart. FIG. 1 shows needles 5 penetrating through the tissue of the patient and entering port 4 so as to make a connection with the patient's central blood supply (i.e., vis-à-vis port 4 and catheters 11). The external (proximal) portions of the needles are connected to blood lines, which, in turn, are connected to the HD machine (not shown in FIG. 1). One blood line is for removal of blood from the patient, and the other blood line is for returning the cleansed blood to the patient, after passing the blood through the dialyzer.

Figure 2:
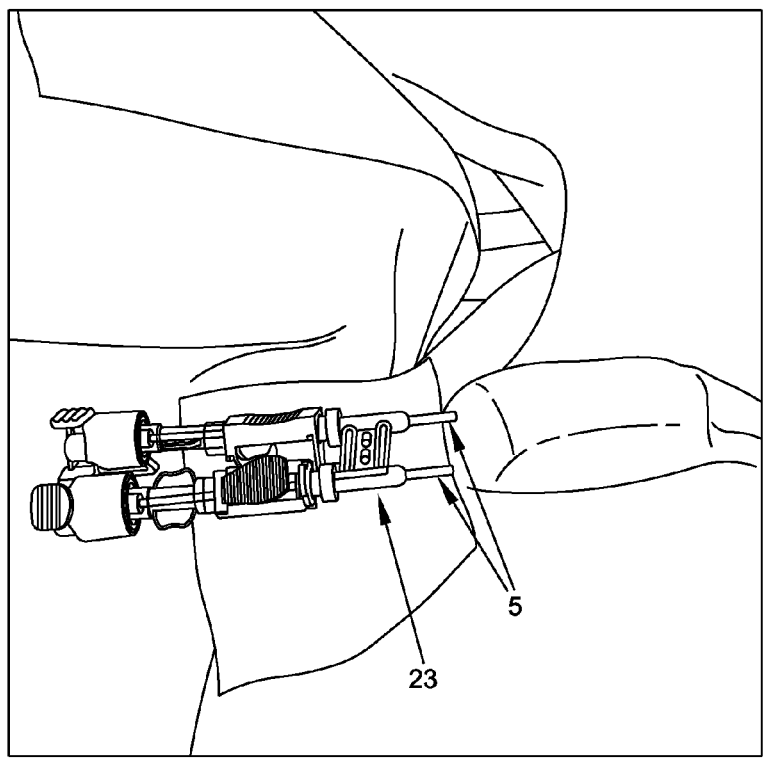
FIG. 2 is a schematic view showing hemodialysis needles accessing an implanted port.

Looking next at FIG. 2, there is shown a photograph of a patient's chest area with a prior art port (i.e., Biolink's Dialock HD port) implanted subcutaneously, and showing use of a percutaneous puncture method for coupling needles 5 to the port. The needles are yoked together with a yoke 100 to form a complete needle assembly 23 for simultaneous insertion and removal of the needles. The patient shown in the figure was extremely thin, so the outline of the implanted port 4 is visible through the skin.

Figure 3:
FIG. 3 is a view showing a patient self-accessing an implanted port.
Figure 4:
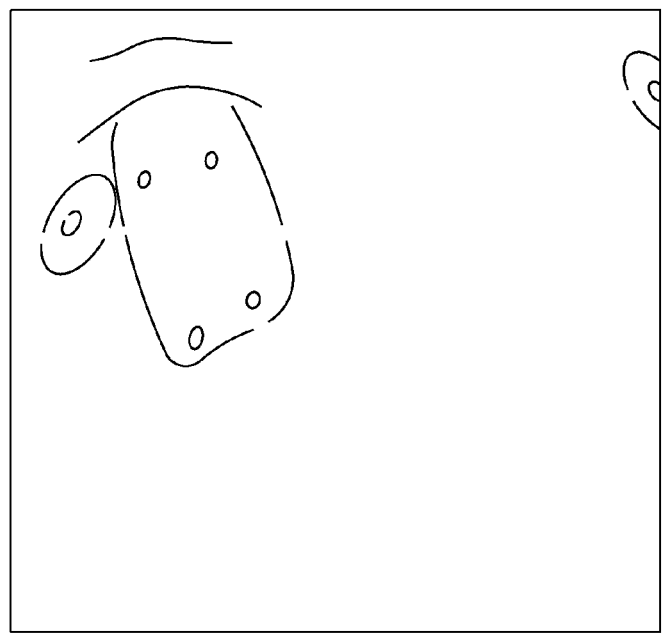
FIG. 4 is a view showing the surface of the skin with buttonholes.

Looking now at FIG. 3 there is shown a photograph of a patient accessing the Dialock port utilizing a prior art "Buttonhole" (BH) technique. The patient shown in the figure was receiving overnight HD treatment 3 times per week in a European clinic. Looking now at FIG. 4, there is shown a photograph of the same patient shown in FIG. 3, but showing a BH-type puncture area after several months of use. The patient self-accessed and "locked" the catheter and BH tract with a taurolidine liquid between HD sessions. The "lock" solution provided prophylaxis against catheter-related infection and local subcutaneous infections.

Figure 5:
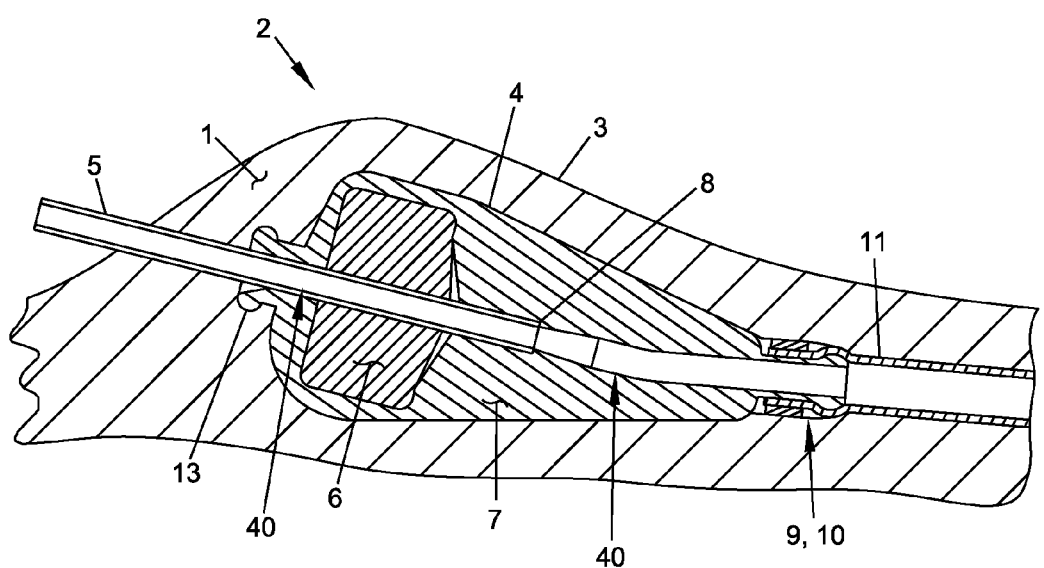
FIG. 5 is a schematic view showing a port formed in accordance with the present invention and installed in a patient.
Figure 8:
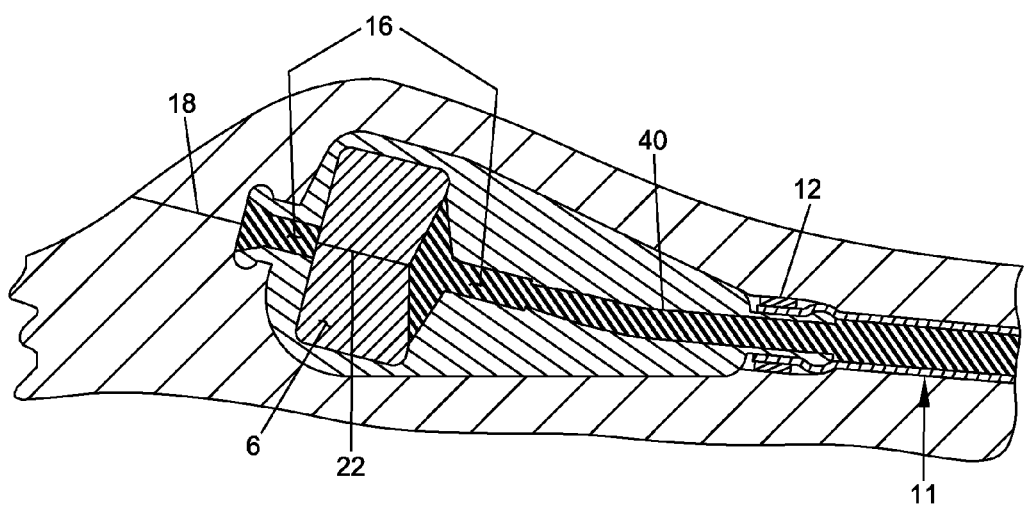
FIG. 8 is a schematic view showing a port formed in accordance with the present invention and installed in a patient.
Figure 8A:
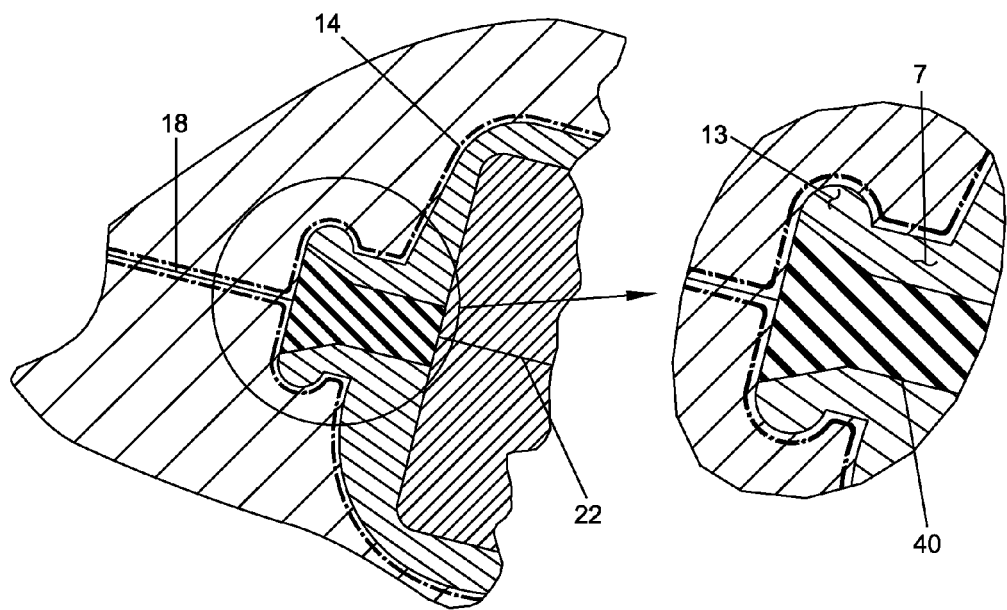
FIGS. 8A and 9 show details of the port shown in FIG. 7.
Figure 9:
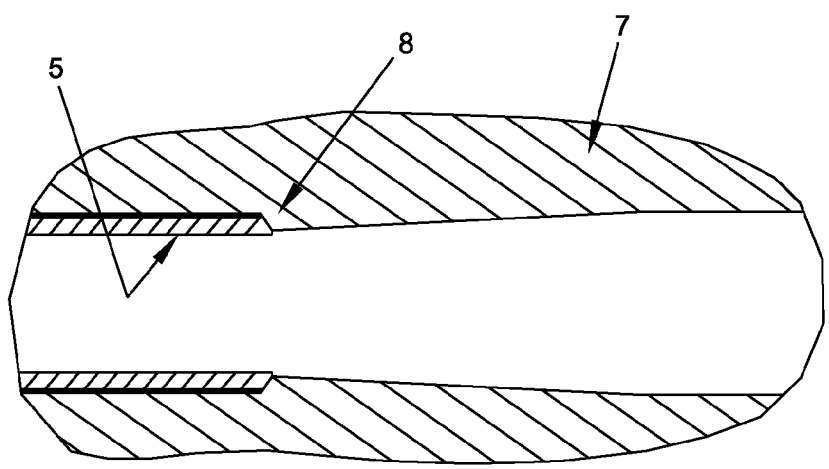

Looking now at FIG. 5, there is shown a cross-sectional view of novel HD port 4 implanted within subcutaneous tissue 1 of a patient. The cross-sectional view cuts through the centerline of one flow passage in an orientation generally perpendicular to the skin FIG. 5 illustrates the condition during an HD session when a needle 5 is coupled to port 4. HD port 4 comprises a housing 7 holding a septum 6. Septum 6 is fabricated out of an elastomeric material incorporating a slit plane or a pierced hole 22 (see FIG. 8) which penetrates through septum 6 co-incident with the needle tract, so that needle 5 is directed through slit 22 in septum 6 during insertion of needle 5. The slit plane or pierced hole 22 formed in septum 6 may take the form of other shapes, e.g., a small-diameter circular hole formed during molding, or produced subsequent to molding by a punching operation, and may, for example, be a line or cross. The purpose of slit plane or pierced hole 22 formed in septum 6 is to establish a controlled "break line" within the matrix of elastomeric septum 6 which is penetrable by a needle 5 by separation of the elastomer matrix, rather than requiring cutting or tearing of septum 6 during insertion of a needle 5. Puncture line 22 (FIG. 8) is positioned to lay co-incident with the line of insertion of needle 5 (FIG. 13). Space is provided within housing 7 to allow deflection of the elastomeric material of septum 6 as needle 5 passes through puncture line 22. Septum 6 is installed within housing 7 of port 4 in a compressive stress state, which is sufficient to prevent blood leakage around or through the septum in the quiescent state (i.e., when no needle 5 is inserted into the port), and during HD operation with needle 5 installed. Housing 7 also comprises an aperture 40 (FIGS. 8 and 8A) and an anchor 13 (FIGS. 8 and 8a). Aperture 40 guides penetration of needle 5 through septum 6. The aperture passage continues in a relatively straight line to a needle stop 8 (FIGS. 5 and 9). Aperture 40 expands to a larger diameter at its distal end in a gradual conical shape, so as to be of the same diameter as the inner diameter of the tube 9 and of catheter 11, integral with housing 7. Tube 9 comprises a bead (or barb) 10 which is larger in diameter than the inner diameter of catheter 11. Catheter 11 is pushed onto the outer diameter of tube 9 (i.e., over bead 10) and a hose clamp is used to create compressive stress around catheter 11 so as to create a sealing force between the elastomeric catheter 11, and tube 9, and thereby prevent catheter 11 from sliding off of tube 9. Catheter 11 is typically connected to housing 7 (i.e., to tube 9) at the time of surgical placement of the port and after placing the distal tips of catheters 11 in or near the right atrium of the heart. Port housing 7 also incorporates an integral anchor site 13, which fixes the distal portion of the novel tissue formation vis-à-vis, and which provides a tract 18 (i.e., called a "tissue tract" herein, and shown in FIG. 7) to guide needle 5 into the entrance of port housing aperture 40. Tissue tract 18 (FIG. 7) joins the tissue layer 14 (FIG. 7) forming around port housing 7. Accordingly, tissue tract 18, aperture 40 and the septum's puncture line 22 are co-incident to each other. Housing 7 further incorporates a physical barrier (i.e., needle stop 8) within the aperture to stop needle penetration after passing through septum 6 and coupling to port 4. Aperture 40 (FIG. 8) starts at the entrance to aperture 40 (formed in anchor 13) and extends along a straight path so as to guide needle 5 through septum 6 to needle stop 8. The blood-flow path continues beyond needle stop 8, with the cross-sectional area of the aperture increasing in a gentle conical fashion, as is consistent with good blood flow dynamics, expanding and bending so that aperture 40 merges with the lumen of catheter 11. Housing 7 includes a friction lock feature (discussed below in connection with FIG. 12) to prevent inadvertent uncoupling of needles 5 from port 4.

The tissue which comprises tissue tract 18 is the same type of fibrous connective tissue comprising membrane capsulation 14 formed around port 4. Tissue capsule 14 and tissue tract 18 are formed naturally around foreign materials within the body (Kouji Masumoto, Genshiro Esumi, Risa Teshiba, Kouji Nagata, Tomoaki Taguchi, Usefulness of exchanging a tunneled central venous catheter using a subcutaneous fibrous sheath, Nutrition (2010) 1-4, [Article in Press as of Aug. 15, 2010]). The present invention describes methods and apparatus for use in conjunction with port 4 to promote natural host-formed connective tissue encapsulation of a foreign body so as to form tissue tract 18, and so as to conjoin a similar type of tissue comprising membrane encapsulation 14 into a contiguous surface comprising 18 (FIG. 8) and 14. The present invention comprises special tools which may be used to form a tissue tract positioned and oriented so as to encourage the attachment of port 4 with tissue tract 18 (FIG. 7) so that alignment of tissue tract 18 and port 4 guides needle 5 to the port's entrance in a line co-incident with the axis of aperture 40 at its proximal end.

Figure 6:
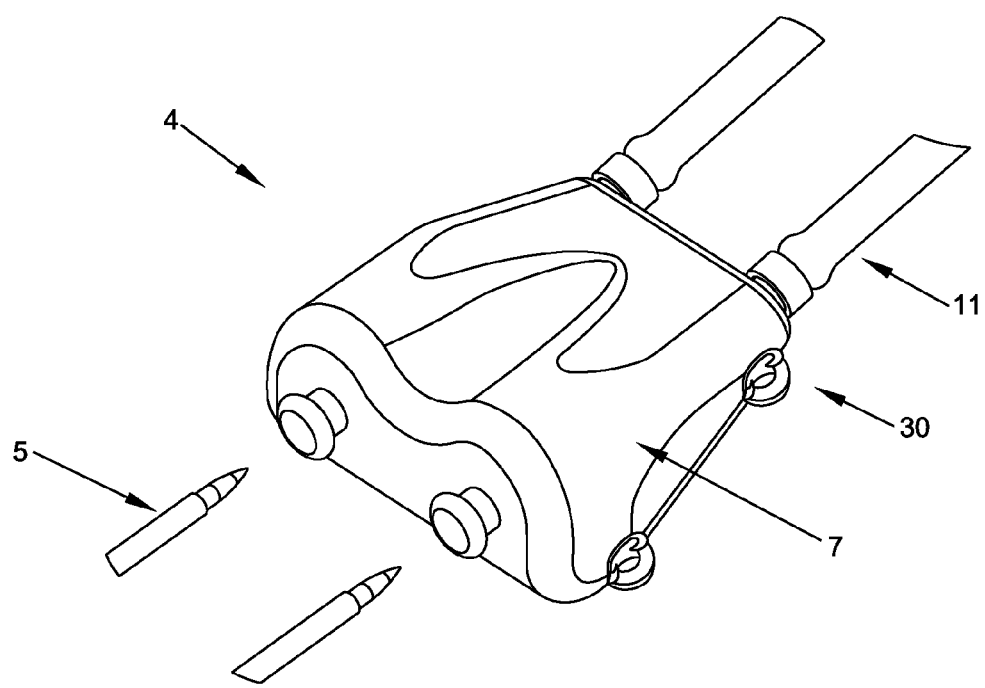
FIG. 6 is a schematic view of a port formed in accordance with the present invention.

Looking next at FIG. 6, there is shown a drawing showing a preferred shape of port 4 without catheter 11 attached. Port 4 is of relatively small height, and with larger width and length (relative to the height of port 4), so as to reduce tensile stress in the subcutaneous tissue and thereby reduce the possibility of "flipping" of the implanted port 4 within the subcutaneous pocket. The height of port 4 is the port dimension generally perpendicular to the general plane of the outer skin surface covering the port. Housing 7 incorporates three or more suture tabs 30 for fastening port 4 to underlying tissue, and for fixing port 4 within the body during surgical placement of port 4.

Figure 7:
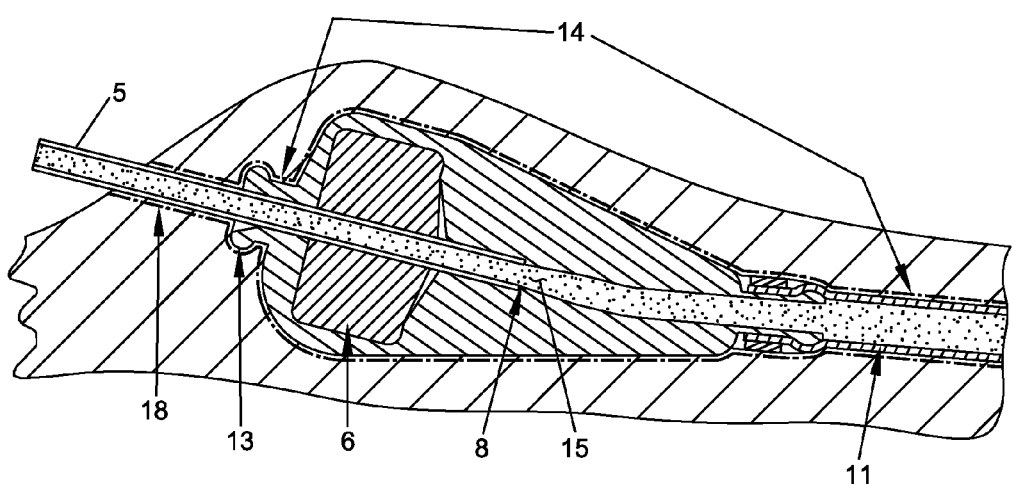
FIG. 7 is a schematic view showing a port formed in accordance with the present invention and installed in a patient.

Looking next at FIG. 7, there is shown a diagrammatic cross-sectional view of port 4 similar to the view shown in FIG. 5, except showing the port during HD treatment, with needle 5 connected and with blood 15 filling the flow passage of port 4 and needle 5. Needle 5 is shown transcutaneously within tissue tract 18 and passing through septum 6, making contact with needle stop 8 and illustrates passage of needle 5 through a tissue tract 18 which is contiguous with the tissue 14 formed around the port 4 (including anchor 13 and catheter 11).

During manual needle insertion, the needle assembly (FIG. 13) enters tissue tract 18 with a conical pointed trocar 25 separating the two sides of the tract. Tissue tract 18 confines and guides needle 5 towards the entrance of the port aperture. Further insertion enables the needle point to spread apart the puncture line 22 of septum 6 without tearing or cutting the septum as the needle advances, until needle 5 reaches a ledge (i.e., needle stop 8) which blocks further insertion of the needle. The coupled configuration of needle 5 against stop 8 presents the best flow geometry for safe blood passage through the needle. Trocar 25 is removed after docking with port 4, so as to create an open needle, and so as to establish a transcutaneous blood flow path. During port placement, catheters 11 are inserted into large blood vessels to provide the necessary blood flow for effective HD. FIG. 7 illustrates tissue 14 formed after placement of port 4, encapsulating port 4 and catheter 11. Similarly, tissue forming a tissue tract 18 is induced to form on a tool placed within the subcutaneous tissue. This tissue formation is a putative host reaction to a foreign body, walling-off the "foreign body" to protect the host (i.e., the patient). The morphology of the tissue layer 14 and tissue tract 18 is strong fibrous connective tissue encapsulating the tool. It is slippery inside the capsule of the fibrous connective tissue, and the outside surface is attached to the surrounding tissue. A tissue tract forming tool 17 (FIG. 12) provides a surface which projects in a straight line from the skin entry point to be co-incident with aperture 40 of port 4, and with tissue tract 18 encapsulating anchor 13 on port 4 so as to guide the needle 5 into aperture 40.

Looking next at FIG. 8, there is shown a cross-sectional view of port 4 similar to the view shown in FIG. 7, except showing port 4 during the quiescent state. FIG. 8 shows needle(s) 5 removed, and septum 6 in a closed condition, sealing off the blood pathway. Antimicrobial gel 16 is instilled into port 4, filling the internal flow passages of port 4 and providing lubrication and prophylaxis. Septum puncture line 22 is in its closed position in the compressive stress state established by the port housing 7. Gel 16 rheology characteristics are tailored so as to resist dislodgement from the passages under the normal host-imposed forces, thereby providing redundant sealing to block blood leakage or air egress in the event of a failure of the sealing integrity of septum 6. FIG. 8 also shows a catheter clamp 12 positioned as a conventional type of catheter clamp is positioned, and which can take many design configurations. FIG. 8 also shows tissue tract 18 in its closed condition. While not seen in FIG. 8, it should be appreciated that antimicrobial gel 16 extends out of port 4 and up along tissue tract 18, preferably all the way to the surface of the skin.

Looking next at FIG. 8A, there is shown a local breakout view of port 4, showing tissue tract anchor 13, which fixes the distal end of the tissue tract 18 to the port entrance. Implanted devices, such as ports, are normally encapsulated with a strong tissue membrane (often called "the tissue capsule") comprising fibrous connective tissue (i.e., tissue layer 14). The present invention comprises methods and apparatus to help establish a similar contiguous capsular formation around the port housing 7 and catheter 11, and a luminal tissue needle tract 18, preferably in the shape of a slit, which envelopes a single closed space inside the body of the patient. Formation of tissue tract 18 is contemporaneous with the formation of the membrane encapsulating port 4, enabling the formation of a single contiguous seamless membrane, with the distal end of the tissue tract fixed to the anchor 13 and to the entrance of port 4. Thusly, anchor 13 fixes tissue tract 18 vis-à-vis port 4 and maintains the alignment of tissue tract 18 relative to port 4 for the guidance of needle 5 to (and into) the port entrance. Other techniques promoting attachment of tissue connective tissue to the outer surfaces of anchor 13 include texturing the outer surface of anchor 13, embedding, coating of anchor 13 surfaces, etc. Alternatively, a mesh material may be attached to the exterior of the port so as to facilitate ingrowth of tissue, producing non-slip conditions which prevent shifting and misalignment between the port aperture 40 and tissue tract 18.

Looking next at FIG. 9, there is shown a local breakout view of port 4 as shown in FIG. 5, showing needle 5 in a fully docked position, contacting a shoulder or ledge (i.e., the needle stop) 8, which stops the needle from further entry into the port aperture. The tip of needle tip 5 is beveled and conforms to the annular stopping surface 8 in the port housing. Needle 5 is positioned so as to enable smooth blood flow transition from the needle's luminal passage to the patient's central blood supply, and so as to minimize damage to the blood. Needle stop 8 provides a solid tactile signal to the surgeon (or the patient, if the patient is self-accessing) when needle 5 achieves the correct position.

Figure 10:
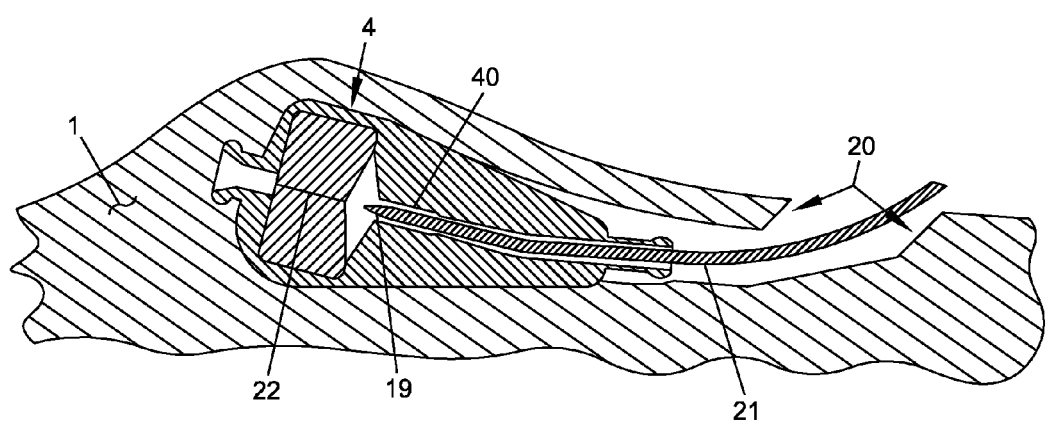
FIG. 10 is a schematic view showing implantation of a port formed in accordance with the present invention.

Looking next at FIG. 10, there is shown a preferred method for eliciting natural tissue tract formation (i.e., formation of tissue tract 18) and alignment of the tissue tract with the port capsule. FIG. 10 is a cross-sectional view similar to that shown in FIG. 5, but at an intermediate point in the surgical placement of the port within the pocket, with surgical incision 20 open. This method produces a properly aligned, straight tissue tract 18 (to be made in a subsequent step), enabling accurate (and repeated) insertion of the needle into the port's aperture. FIG. 10 also shows the puncture line 22 of closed septum 6. A penetration tool 21, with conical tip having a small radius point 19 disposed at the distal end of the penetration tool, may be used for tunneling through subcutaneous tissue 1. Penetration tool 21 is shown inserted into and through the distal portion of the aperture of port 4. The tissue tract path line is created by pushing penetration tool 21, such that the penetration tool advances, retrograde, through port 4 and continues through the subcutaneous tissue to the outside of the patient (i.e., the surface of the skin). Penetration tool 21 penetrates subcutaneous tissue in a similar fashion to that of the tunneling tool commonly used to create a tunnel for catheter placement. Aperture 40 of port 4 guides penetration tool 21 so as to penetrate the subcutaneous tissue in a straight line trajectory, i.e., exactly along the line to be followed by tissue tract 18. Piercing of the epidermis may be aided, if necessary, by a scalpel stab from the outside of the patient. Penetration tool 21 is then withdrawn, and tissue tract forming tool 17 (FIG. 12) is inserted into the penetration path, and into the aperture 40. Tissue tract forming tool 17 presents a "foreign body" platform to the host (i.e., the body of the patient), which induces tissue encapsulation of tissue tract forming tool 17.

Initiating formation of tissue tract 18 at the time of placement of port 4 enables control of various factors which may affect tissue tract performance, including location of port, pocket size, tissue tensile stress level, direction of stress in the subcutaneous tissue surrounding tissue tract and the precision of the alignment between tissue tract 18 and port 4. Creation of tissue tract 18 contemporaneous with the placement of port 4 also helps ensure the formation of a seamless contiguous inner surface of the membrane, thereby reducing cavities between the membrane capsule and port 4, and avoiding a "safe harbor" for microbes (i.e., thereby reducing the risk of infection).

Penetration tool 21 may be a separate (i.e., ancillary) device, or it may be pre-inserted into the port assembly as shipped from the factory. The preferred method of creating the initial penetration line for tissue tract 18, and for the placement of the platform for the formation of tissue comprising tissue tract 18, is described in the following steps (however, it is recognized that a healthcare professional may modify, add or eliminate steps, and/or change the sequence of the steps, according to personal preference, without departing from the teachings of the present invention). Initiation of tissue tract formation is performed around the midway point of the port placement procedure, along the following guidelines:

(1) Verify that a sufficient space in the pocket allows port 4 to fit inside of the pocket without high tensile stress forming in the overlaying tissue.

(2) Fix the port to the underlying tissue by suturing port 4 through its suture attachment points 30 which are formed in the port's housing 7.

(3) Temporarily close incision 20 using clamps or other suitable method known to those of ordinary skill in the art.

(4) Advance penetration tool 21 through the subcutaneous tissue until the distal end of penetration tool 21 protrudes through the surface of the skin A surgical scalpel or needle may be used to assist skin piercing from outside of the patient.

(5) The suture pocket incision is closed. Puncture tool 21 will remain in place to serve as a guide for insertion of the tissue tract slit forming tool 17.

(6) Determine the direction of minimal tensile stress in the tissue surrounding penetration tool 21. Tissue tract slit-forming tool 17 (FIG. 12) may then be inserted along the path of the puncture wound with the elongated distal rod portion of tissue tract forming tool 17 directed to enter into aperture 40 of port 4. Alignment of the flat wings on the tissue tract slit-forming tool 17 should be perpendicular to the minimal tensile stress vector formed in the overlaying subcutaneous tissue. The objective of this alignment is to ensure that the tissue minimally separates from the flat surface of the slit tool 17.

(7) Tissue tract slit-forming tool 17 should be held in place for a few days with an external suture or other means, until a robust tissue tract 18 has been established.

(8) Tissue tract slit-forming tool 17 may be removed as is necessary to perform HD treatment and then re-inserted to re-establish the tool's subcutaneous position and to complete tissue tract formation.

It is recognized that techniques and tool configurations may be modified to practice the tissue tract formation methods without deviating from the scope of the present invention. For example, the tip of penetration tool 21 may be releasably attached to the tissue tract penetration tool 21 by a fastening technique, which allows the tip to be removed and a tissue slit tool attached in place of the puncture tool. Pulling on the proximal end of penetration tool 21 will pull the tissue tract slit-forming tool 17 into and through the puncture tract, and into aperture 40 of port 4. The tissue tract slit-forming tool 17 may produce some enlargement of the initial puncture tract.

The tissue tract slit-forming tool may be oriented so as to produce a slit, aligned in the direction providing minimum tendency for opening of the slit by tensile stress formed in the epidermis and in the underlying subcutaneous tissue. When tissue tract 18 is formed, tissue tract slit-forming tool 17 may be removed. The outer surfaces of tissue tract slit-forming tool 17, which are in contact with subcutaneous tissue during use, can also be treated so as to assist in the formation and proliferation of connective tissue.

The tissue comprising tissue tract 18 is a type of membranous fibrous connective tissue which forms naturally around (i.e., encapsulates) "foreign body" materials residing in subcutaneous tissue of the human body. Materials known to promote or increase proliferation of connective tissue formation include, but are not limited to, methylene blue, fibrin glue and various metals and polymers which elicit strong "foreign body" reactions in a host (e.g., a human body).

Figure 11:
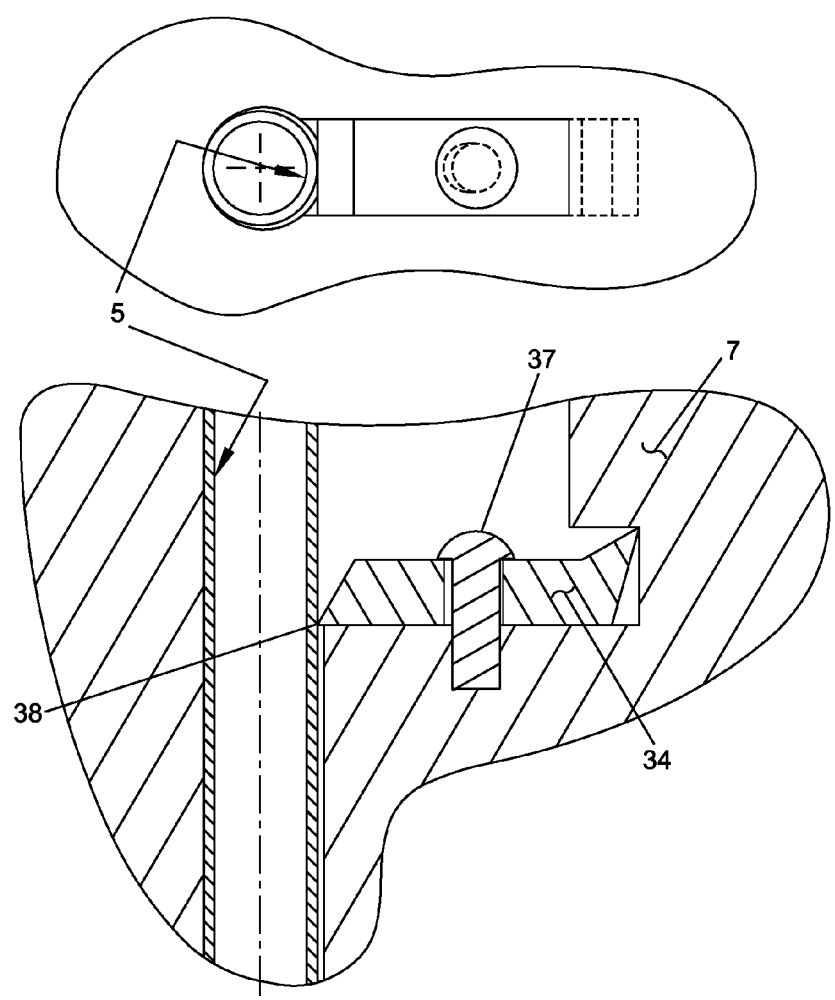
FIG. 11 is a schematic view showing a releasable lock for securing a needle to a port.

Looking next at FIG. 11, there is shown two views: (i) a top view looking head-on into housing aperture 40, with needle 5 inserted into port 4, and (ii) a lower side view perpendicular to the top view. These views schematically detail a needle locking feature which reduces risk of inadvertent disengagement of needle 5 from port 4. The locking feature increases the sliding friction of a needle 5 against a pawl 38 by producing high contact stress, produced with a relatively low normal force, by making the contact area very small (i.e., by making the contact area as small as that of a sharp knife edge contacting a surface). In the context of the present invention, a small diameter needle 5 may be placed into contact with a knife edge pawl 38 under a small applied lateral force, so as to create high contact stress and so as to require relatively high axial drag force to move needle 5 along its longitudinal axis.

In a preferred embodiment, pawl 38 is positioned near the aperture entrance in the port housing 7 such that needle 5, in its free state, (i.e., when needle 5 is not coupled to a second needle, as is the case when two needles are joined to form needle assembly 23) may be inserted and removed without making contact with the "knife edge" of pawl 38. A small lateral force can be generated which pushes needle 5 into contact with the "knife edge" of pawl 38, when needle 5 is used in conjunction with a needle attachment feature (i.e., when joined together in needle assembly 23), which is a modified configuration from prior Dialock needle accessory (see FIG. 2 for a prior art paired-needle design). With both needles inserted into port 4, a small lateral force is created which may be used to bring the proximal ends of needles 5 closer together and thereby engage a lock tab on each needle. See FIG. 2. The lateral movement of needles 5 causes each needle to bear against the respective "knife edge" of each of pawls 38 disposed in port 4. When attached together, the force required to overcome the frictional drag between the pawl and needle is considerable. Releasing the small lateral force is accomplished by disengagement of the needle attachment tab, which thereby enables easy withdrawal of the needles from the port. It should be appreciated that in the present invention, pawl 38 is composed of a material harder than the material which forms needle 5. Pawl 38 is fastened loosely to housing 7 of port 4 (e.g., by a rivet or screw 37).

Alternatively, the friction lock shown in FIG. 11 can comprise a pawl 38 which is allowed a small degree of rotation induced by the frictional force as the needle is being pulled out of the port. The rotation increases contact stress resulting in a higher frictional force. A similar mechanism is the well-known screen door closer "hold open" feature, which prevents the piston shaft from moving, and thereby keeps a door open (e.g., U.S. Pat. No. 4,777,698, Sleeve for holding door closer 1988).

Figure 12:
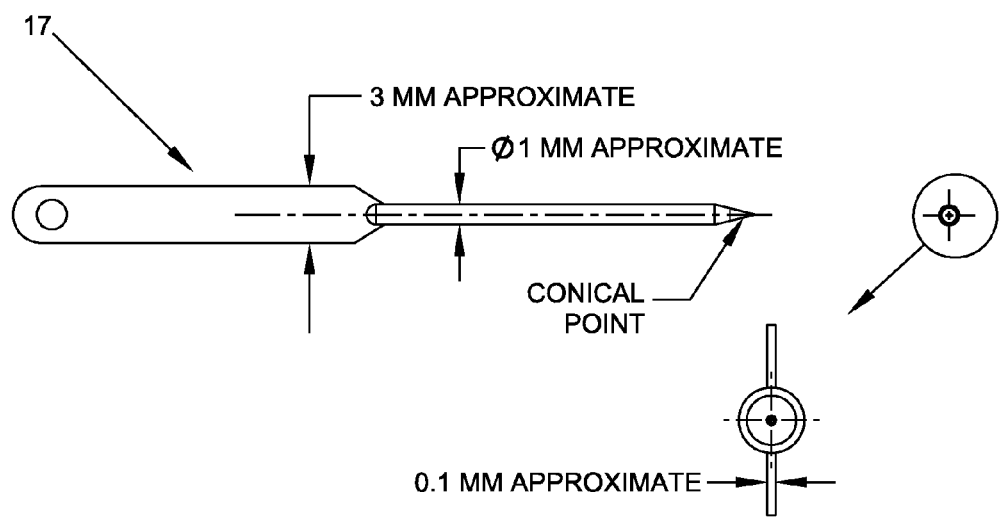
FIG. 12 is a schematic view of a tissue tract forming tool formed in accordance with the present invention.
Figure 13:
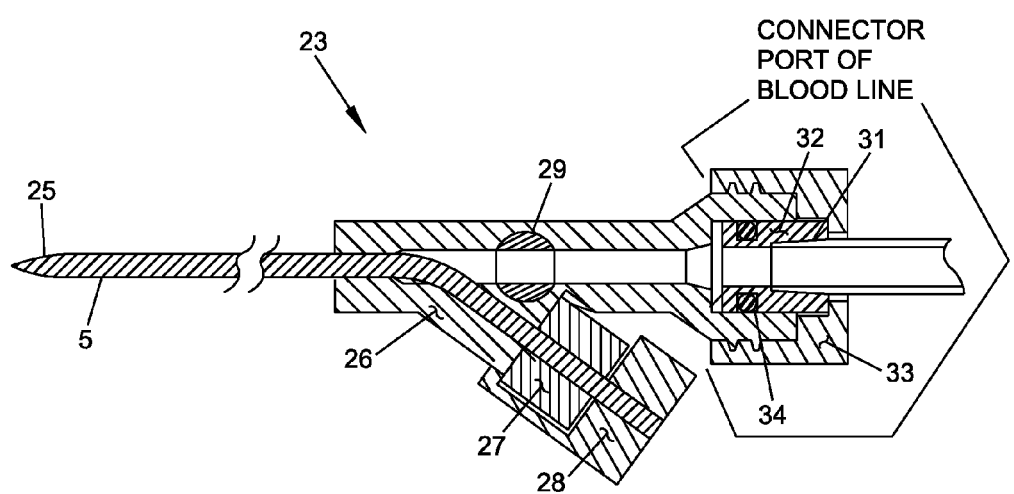
FIG. 13 is a schematic view of a needle assembly formed in accordance with the present invention.

Looking next at FIG. 12, there is shown a sketch of a novel tissue tract forming tool 17. Tissue tract forming tool 17 is inserted into the initial puncture site of the tissue tract as described in FIG. 10 so as to form a slit-shaped tissue tract comprising natural tissue. Tissue tract forming tool 17 essentially serves as a "foreign body" platform enabling connective tissue encapsulation. A preferred technique aligns tissue tract forming tool 17 in such a plane that the tensile stresses within a patient's tissue are minimal, thereby preventing opening of the separation formed by the slit shape, and thereby reducing the tendency for contamination (i.e., preventing microbes, foreign bodies, etc., from entering into tissue tract 18).

Additional prophylaxis is provided by the "gel lock" which, in combination with the alignment of tissue tract 18, establishes a multi-pronged defense against tissue tract infection. Pressure bandaging may be a further technique in closure protection, i.e., a pressure bandage may be applied to the skin-side end of tissue tract 18, whereby to close off the entrance to the tissue tract between dialysis sessions. In one preferred form of the invention, the tissue tract is filled with an antibacterial gel prior to bandaging the tissue tract 18 at the skin surface. Dimensionally, tract forming tool 17 should have a round diameter approximately the same diameter as the diameter of the needle to be inserted into port 4, and tract forming tool 17 should have a width (W) of about 3 to 10 times larger than D. This additional width to tissue tract forming tool 17 may be provided by adding radially-extending wings to the body of tissue tract forming tool 17.

Looking next at FIG. 13 there is shown a cross-sectional view of a novel needle assembly 23, used for coupling with an implanted HD port. Needle assembly 23 comprises a bloodline connection, with improved blood flow dynamics and safety. A hypodermic needle 5 is permanently attached to a needle housing 26, which is preferably formed out of a medical grade polymer produced by injection molding. Needle 5 may be insert-molded into needle housing 26 during the molding or needle 5 may be subsequently bonded to the housing. Needle 5 has a perpendicular beveled tip conforming to the geometry of needle stop 8. Needle 5 is preferably of about 14 to 16 gauge size, as is suitable for HD blood flow and HD therapy. A trocar 25, comprising flexible polymer rod, is shown installed into needle housing 26 with the tip of trocar 25 protruding beyond the distal end of needle 5. Trocar 25 includes a conical tip, which has no cutting edges or points, and which cannot puncture (i.e., damage) or cut tissue tract 18 or the septum's puncture track 22. Penetration proceeds by displacement and deflection of passage material inside of tissue tract 18. Radial clearance between needle 5 and trocar 25 shall be as small as practical. Tip shapes other than conical are suitable if they penetrate tissue tract 18 and puncture line 22 without cutting. A cap 28 is permanently attached to the proximal end of trocar 25 and comprises means for permitting trocar 25 to be locked into needle housing 26, and to be removable from the housing 26, as desired. A seal fitting 27 is attached to needle housing 26 and may be a commercially available seal assembly, which seals off the passage if no object (i.e., if no trocar 25) is inserted. Seal fitting 27 allows trocar entry, and provides sealing around the trocar. Alternatively, a plug 35 (not shown) may be used in place of seal fitting 27. Plug 35 is a rod similar to the trocar but is truncated such that it does not enter the flowing blood path but creates a relatively seamless surface with the blood pathway lumen (i.e., plug tip forms a cylindrical surface matching the luminal surface of the blood pathway in the interior lumen of needle 5) to minimize blood flow perturbation at the intersection of the trocar and blood path. A rotary plug valve 29 is disposed intermediate the length of needle 5 and is formed within needle housing 26. Plug valve 29 may be used to control the flow of blood through needle 5. Preferably rotary plug valve 29 is a low-cost, two-position on/off plastic valve of the type commonly used in disposable syringe applications. The closed valve separates and seals a blood line 33 (i.e., the circuit to/from an HD machine) from the trocar path and the patient during the coupling of the access and during the prophylactic lock instillation or during withdrawal of the prophylactic lock installation. Trocar 25 may be removed and a plug (not shown) may be inserted, fastened and sealed (i.e., in a fashion similar to the means employed for fastening and sealing the trocar) before treatment starts. The rotational locking feature of plug 35 aligns the distal end of the plug such as to provide a smooth path inside the blood circuit.

During HD treatment, plug valve 29 is open so as to allow blood flow from an HD machine to the patient, or to allow flushing of the lines after HD is complete. Ball valves, as well as other types, may be incorporated as alternatives to the plug valve. Elements 30, 31, 32 and 34 are components comprising connector fitting components attached to bloodline tube 33 and are used to couple needle assembly 23 to bloodline 33. The figure illustrates the coupled condition. This connector configuration eliminates the standardized luer coupling design which causes a.) flow perturbation at the sharp change in flow cross sectional area and b.) blood leakage from even small loosening of threaded fastener 34. The design of the present invention comprises an optimized flow interface with gentle flow area convergence to needle 5 and tolerates considerable loosing of threaded fitting without blood loss. A simple anti-rotation feature is incorporated to prevent inadvertent separation of threaded fitting 34 from housing 26.

HD Implantable Port

The novel HD port 4 of the present invention is of a simple design, comprising a septum closure 6 capable of withstanding a large number of penetrations by a large needle 5 and suitable for HD blood flow. HD port 4 is able to withstand a large number of needle penetrations by eliminating damage to septum 6. This is achieved by eliminating cutting and wear produced by needle piercing. This design provides for a.) non-cutting needle penetration, b.) penetration through septum 6 along the same line for each penetration and c.) lubrication so as to lower the friction between needle 5 and the septum 6 elastomer. This avoids the damage from intersecting cuts formed through septum 6 when subjected to randomized puncturing and high wear. The ancillary needle 5 is blunted and made non-cutting, i.e., so as to pass through subcutaneous tissue and the epidermis via novel tissue tract 18, and to enter the port aperture 40 and penetrate through septum 6, thereby creating a transcutaneous passage for fluid flow. Lubricant gel reduces the frictional, interfacial rubbing between needle 5 and septum 6 surfaces during penetration of the septum by the needle, which reduces the force needed to penetrate septum 6 and reduces wear on the septum. Septum 6 is compressed in the installed condition, so as to produce a compressive stress level for effective sealing around the needle while in a coupled condition, and so as to produce closure of the needle penetration line 22 upon withdrawal of needle 5. Extraction of the needle instantly "shuts off" passage to a patient's blood supply and prevents even small amounts of bleeding during, or after, needle withdrawal. The design has few components, is robust and holds needles securely and rather rigidly when compared to AVF or prior HD ports, thereby helping to reduce stretching of tissue tract 18 as may be caused by side movement of needle 5. During HD treatment, septum 6 seals around needle 5 and prevents external blood leakage. This design is inherently tolerant of considerable axial movement, without incurring any leakage, and is therefore a considerable improvement over prior HD ports.

Port aperture 40 guides needle 5 so as to penetrate compressed septum 6 in an exact line through septum puncture plane 22, in line with aperture 40 of port housing 7, by exerting small insertion force to penetrate tissue and port closure.

The shape of the flow passage enables excellent fluid (i.e., blood) flow characteristics, without turbulence, during an HD treatment. Port 4 incorporates a needle stop 8 so as to provide positive tactile feedback and enable correct axial position of needles.

The composition of prophylactic gel 16 reduces wear from repeated penetrations of septum 6 and of tissue tract 18. The antimicrobial action of gel 16 provides prophylaxis to port 4 and to tissue tract 18. Gel composition 16 may be adjusted to provide redundant sealing in event of septum integrity failure during the quiescent period. Needles may also be lubricated (e.g., with the prophylactic gel) prior to insertion.

The aspect ratio of port 4 (i.e., having a large base and a small height dimension) combined with tie-down suture anchor points, help keep the port in a stable position, so as to maintain alignment of the tissue tract 18 with the aperture 40 of the port.

Tissue tract anchor 13 fixes the distal end of tissue tract 18 to the entrance of port 4 and enables joining of the membrane of tissue tract with the tissue capsule 14 surrounding port 4, thereby helping to establish and maintain the alignment required for needle guidance into the port. The low profile of port 4 reduces tensile stress in the subcutaneous tissue around tissue tract 18, helping to maintain closure of the tissue tract when the tissue tract is in its quiescent condition. Needles 5 may enter port 4 at an acute angle, and may have a relatively long, supported length within the body of the patient, rather than protruding unsupported and perpendicular to the body of the patient. This improves security from inadvertent needle dislodgement, and allows a preferred angle for fastening of needles to the host.

Stagnant (i.e., "dead") flow regions within port 4 are minimal, allowing effective blood flushing, which helps preclude clot formation within the port. Port 4 incorporates a simple friction lock (i.e., powl 38), which holds needles 5 in place during HD to reduce interrupted operation during HD.

Insertion of needle 5 requires that the tip of the needle enter the tissue tract 18 at an easily visible site on the patient epidermis at the proximal end of the tissue tract leading to the entrance of port 4. Continued insertion of needle 5 into port aperture 40 guides the needle to penetrate septum 6 until the needle is stopped by the internal needle stop 8. This provides a positive tactile feedback to the user that needle 5 is in the proper position.

Port housing 7 incorporates an anchor 13 for fixing tissue tract 18 to aperture entrance 40. Precise needle puncturing is made easy, as tissue tract 18 is aligned co-incident with aperture entrance 40 and therefore with septum penetration line 22. This line is established during implantation of port 4. The design of port 4 provides for retrograde entry of a penetration tool 21 which allows the port aperture to guide the tool to create an initial penetration path, which is in line with port aperture 40 of the implanted port 4. The method and the tools for creating this initial penetration for the subsequent formation of the tissue tract are discussed herein.

Implantation of port 4 and the piercing of the tissue to establish tissue tract 18 are performed in a single minimal intervention, unlike as is performed in AVF creation. This enables the surgeon to make the determination of port location and orientation so as to satisfy the unique conditions dictated by the patient's body type, catheter insertion requirements and accessing needs.

Tissue Tract

Formation of the tissue tract begins by placement of a "foreign body" platform, referred to herein as tissue tract forming tool 17, within the patient's subcutaneous tissue 1, thereby enabling fibrous connective tissue formation of a desired shape and morphology around the tissue tract forming tool 17, which will act as a guide pathway for needle 5. This method provides a precisely aligned pathway coincident with port aperture 40, and enables tissue tract 18 to adjoin the encapsulating tissue 14 surrounding port 4, and to encapsulate anchor site 13 on the port to maintain alignment of tissue tract 18 with port aperture 40. This is achieved, most preferably, by creating the conditions for tissue tract formation contemporaneously with the implantation of port 4. The surgeon's preparation time for establishing the tissue tract during placement of port 4 is minimal, and the total time for the surgical aspects of implanting the access system is considerably shorter than the surgical time required for AVF creation.

Preparation for the natural formation tissue tract 18 in the body of the patient is performed during the port placement procedure. This enables selection of port placement location, selection of pocket size for retaining the port and tissue tract length to be adjusted by the surgeon, taking into account patient accessing needs and tissue tensile strain affects. Formation of the membrane of tissue tract 18 contemporaneous with the formation of the natural tissue membrane 14 forming around port 4, favors similar tissue morphology, with contiguous and seamless tissue in the tract and port capsulation membrane area. The entry passage of port 4 is accessed through a member which protrudes from the port's housing, and which comprises an anchor site 13 for tissue tract formation, ensuring that the distal portion of tissue tract 18 is fixed to port's aperture 40. Tissue tract 18 comprises a membrane tissue tract, formed out of a strong, thin membrane tissue, formed in the shape of a slit, and having a smooth slippery interior surface. The thickness of the membrane is controllable by the surgeon, as well as the orientation of the slit within the host tissue. The slit shape tends towards closure in the quiescent condition, which can be assisted with a bandage. The shape of tissue tract 18 and its smooth, slippery surface enables easy sliding and deflection during penetration by a conical pointed needle 5, which is blunted to prevent cutting or piercing of tissue.

Prior "scar tissue" etiology, formed by repeated subcutaneous tissue trauma using cutting HD needles and subsequent healing, produces a tissue structure that is neither shaped nor orientated for optimum functionality (as scar tissue is not controlled sufficiently to ensure a precise aligned tract coincident with port aperture 40 and would not be fixed to port 4 for long term precise alignment). Placement of port 4 is relatively simple comprising steps of:

1. Placement of catheter 11 in a blood vessel and placement of tunneling catheters to the port site;
2. creation of a subcutaneous pocket;
3. attachment of catheters 11 to port 4;
4. suturing port 4 to the underlying fascia; and
5. Closing the pocket.

The preferred time for creation of tissue tract 18 is after step 2 of port placement, which enables direct visual access of port aperture 40 and of the end points of tissue tract 18, and allows the surgeon to control port position, enabling retrograde insertion of penetration tool 21 into port 4. Penetration by penetration tool 21 through the subcutaneous tissue is performed by pushing the tool through port 4, so as to enter the subcutaneous tissue, and by tunneling through the tissue in a manner similar to an HD catheter tunneling procedure. Piercing of the epidermis may be aided with a scalpel stab. A tissue slit-forming tool 17 is inserted along the previously made puncture path, and is inserted into the entrance of port 4, until tissue tract forming tool 17 hits a stop (i.e., needle stop 8). The tissue tract forming tool 17 is used for inducing tissue to form an encapsulating tunnel which conforms to the geometry of tissue tract forming tool 17 (i.e., a small slit) so as to become the needle tract. The procedure may encompass several design/method variations. For example, tissue tract forming tool 17 may be attachable to penetration tool 21 after the penetration tool penetrates the subcutaneous tissue, and then the penetration tool can be withdrawn so that the penetration tool pulls the tissue tract forming tool through the subcutaneous tissue and into port aperture 40. Alternatively, rather than using the actual port 4 as a template, a tool mockup of port and aperture can be fabricated to guide the trajectory of penetration tool 21.

Other methods of creating a straight puncture line in alignment with an implanted port are envisioned, including the creation of the subcutaneous tissue tract 18 prior to placement of port 4, e.g., by inserting a probe percutaneously from outside, and subsequently, during port placement, e.g., by aligning the port so that the probes may align and enter port aperture 40. Subsequently, the port pocket is closed, and tissue tract forming tool 17 is held in place by tape, suture or other means to enable the tissue encapsulation to manifest.

Preferably, patients may begin HD within a few days of placement of port 4 via the formed tissue tract 18. If immediate HD is required, the tissue tract forming tool 17 may be removed for an HD session and then replaced after the HD session is complete. Redundant catheter access placement during AVF or AVG construction to allow immediate HD treatment is not required with use of the present invention.

Forming tissue tract 18 into a preferred slit shaped membrane replicates the etiology of tissue formation of the membrane enclosing the implanted port 4. The luminal tract of tissue tract 18 is of connective tissue and is controllable with respect to thickness, shape and surface smoothness by the surfaces of tissue tract forming tool 17. Tract characteristics can be altered by a.) tissue proliferative agents to enhance connective tissue formation and/or b.) selection of a "foreign material" interface, or base tool composition, and its shape.

Tissue tract 18 is strong, durable and slippery on the inner surface and attached to the host subcutaneous tissue on the outer surface.

Tissue tract forming tool 17 may be formed with radially extending "wings", which can help to facilitate the formation of tissue tract 18 in the geometry of a slit. Furthermore, the "wings" of tissue tract forming tool 17 may be treated so as to provide enhanced connective tissue growth by use of proliferative agents. The "winged" tissue tract forming tool 17 enables a preferred shape of the connective tissue forming into a flat thin slit tract easy to effect closure. The angular orientation of the winged forming tool within the subcutaneous tissue is selected so as to produce a slit which is acted on by the subcutaneous tissue moving towards tissue tract 18 and thereby effecting closure of the tissue tract. Examples of tissue proliferative agents include methylene blue and fibrin glue to name a few examples. (Singh-Ranger G. Mokbel K. Capsular contraction following immediate reconstructive surgery for breast cancer—An association with methylene blue dye. International Seminars in Surgical Oncology 2004, 1:3 [Bio Med Centeral—Open Access]); (Dewan P A, Condron S K, Morreau P N, Byard R W, Ter J, Plastic migration from implanted centeral venous access devices. Arch Dis Child 1999; 81: 71-72); (Egbert Jan Oliver ten Hallers. Assessory Device Fixation for Voice Rehabilitation in Laryngectomised Patients. PhD thesis—University Medical Center Groningen, University of Groningen, Groningen, the Netherlands 2006)

A preferred method to perform port placement and tissue tract creation comprises following:

1. Create a pocket for port 4, sized to minimize tensile stress in tissue overlaying port and leaving a sufficiently thick layer of tissue in order to provide a sufficiently long tissue tract 18 so as to act as a support for needle 5 and to act as barrier to contamination (i.e., infection);

2. Insert port 4 into a favorable position within the pocket and fasten down the port to underlying tissue in 3 or more places utilizing suture tabs 30 formed in housing 7 of port 4;

3. Insert tissue penetration tool 21 retrograde into port 4 via catheter connection tubes;

4. Position and temporarily fix the tissue over the port, simulating the condition of epidermis tissue after closure of the pocket;

5. Advance the tissue penetration tool through the port's septum, penetrating subcutaneous tissue and the epidermis, to exit the body of the patient. Piercing the epidermis can be aided by a scalpel stab;

6. Replace the tip of tissue penetration tool 21 with slit-shaped tissue tract forming tool 17, and orient the flat area of the slit to be perpendicular to the direction of the minimal tensile stress vector in the subcutaneous tissue surrounding the puncture line, so as to minimize the opening tendency of the slit. Pull tissue tract forming tool 17 so that it enters the puncture line created and into the port aperture and advance it until it is blocked by the port housing stop;

7. Remove the probe portion of the slit forming tool, leaving in place the flattened portion of the slit forming tool;

8. Secure tissue tract forming tool 17 in place by use of tape or other fastening means outside the body of the patient;

9. Open the pocket and connect catheter 11 to port housing 7. Close the pocket incision;

10. The tissue tract forming tool 17 will remain until tissue tract 18 is healed, or until (and if) an HD treatment is required before healing is complete. If HD treatment is required before the tissue tract is healed, tissue tract forming tool 17 may be removed to allow HD treatment, and then it may be returned to its subcutaneous position to allow further tissue tract formation. From time-to-time, an antimicrobial substance (preferably in gel form) may be instilled into the still-forming tissue tract 18;

The geometry of tissue tract 18 may comprise a slit, which enables a closed tissue tract when needle 5 is removed, and the closing of tissue tract 18 can be augmented by bandaging between HD sessions. Instillation of antimicrobial gel 16 helps block entry of contamination, and provides active prophylaxis to prevent biofilm formation within tissue tract 18, and reduces infections associated with the tissue tract. After formation of tissue tract 18 and its use, the prophylactic gel lubricant 16 can be modified to include an antiproliferative API to prevent connective tissue growth and stop adhesions from forming within the tissue tract. This helps to maintain tissue tract 18 in a separable condition suitable for receiving blunt needles without penetrating, tearing or cutting the tissue tract. Taurolidine or other taurinamide derivatives and/or other methylol transfer agents such as Cyclo-taurolidine and/or Taurultam or other bioequivalent antiproliferative agents including APIs used in cardiac drug eluting stents for prevention of stenosis have demonstrated antiproliferative action.

A specially formulated visco-elastic gel 16 may be instilled into the port and the tissue tract as a lock between HD treatments, providing redundant sealing off of patient's blood supply in event of septum integrity failure.

Gel Lock

The gel "lock" 16 lubricates and acts as a carrier for antimicrobial APIs to enhance utility by:

1. lowering friction between needle 5 and septum 6 so as to enable a vastly longer puncture life for a septum closure of a new HD port and for the tissue tract 18 for enhanced self-accessing;

2. provides an antimicrobial "lock" for prophylaxis of catheter 11, the port passage portion of the access system and tissue tract 18 against infection;

3. provides visco-elastic characteristics so as to provide a redundant seal to the septum 6 and tissue tract 18;

4. coats tissue tract 18 to ease patient accessing, and to help block the entry and the growth of microbes within the tissue tract;

5. provides a prophylactic and lubricious coating for needles 5 used with a conventional BH tissue tract and with other ports;

6. provides a gel 16 comprising hydrophobic properties, which can provide superior protection during swimming or other water immersion activity when instilled in tissue tract 18. These gels will not dissolve when in contact with water, thereby maintaining protection from entry of non-sterile aqueous fluids.

7. provides a gel matrix carrier tailored to specific rheological values, which can provide optimized performance for particular dimensional characteristics of catheters and their particular medical use. Three examples include:
   a. to resist movement of a gel within catheter 11 requires that gel 6 shear strength be sufficient based on the magnitude of the shear force acting on the gel, which shear force is a function of catheter's diameter and length and the host mechanical forces that are imposed,
   b. to affect a practical time to move gel 6 though a catheter 11 with a syringe requires specific range of gel viscosity, shear thinning characteristic and a limitation on the shear yield strength based on catheter geometry.
   c. Providing resistance to motion and other mechanical forces between treatment and enable removal of gel in a catheter with a syringe requires a viscoelastic gel (i.e.

also called thixotropic gel) which also satisfies the considerations described in "a" and "b" above.

Gel 6 may be a carrier of several APIs which enhances the utility of the gel for ancillary or other medical procedures. The following are useful API additives for medical formulations for use with the port/catheter assembly or a blood catheter:

1. Antimicrobial agents, including taurolidine and other taurinamide derivatives, and/or menthol donor compounds, including cyclotaurolidine (20080027043 Herdeis), various medically safe alcohols, EDTA compounds, antibiotics and medically approved biocides and bacteriostatic agents and agents, for example, those taught in U.S. Pat. No. 6,350,251 Prosl.

2. Anticlotting agents, anti-platelet-aggregation drugs, and clot lysing agents.

3. Imaging intensifiers, including air bubbles for ultrasound instruments and opacity enhancers for X-ray type equipment. Gel 6 enables higher concentration of a contrast media than a liquid to enable better defined images. Gels may also be formulated as locks to prevent spillage into the patient's bloodstream. (Polaschegg H D, Loss of Catheter Locking Solution Caused by Fluid Density, ASAIO J 2005; 51: 220-5).

4. Antiproliferative agents which reduce formation of extra cellular matrix such as smooth muscle cell and connective tissue cells, include a.) taurolidine and other taurinamide derivatives, or other related menthol donor compounds including cyclotaurolidine (20080027043 Herdeis) and b.) antiproliferative coating for heart stents, including drugs such as sirolimus, paclitaxel, dexamethasone and zotarolimus (Greenhalgh J, Hockenhull J, Rao N, Dundar Y, Dickson R C, Bagust A. Drug-eluting stents versus bare metal stents for angina or acute coronary syndromes. Cochrane Database Syst Rev. 2010 May 12; 5:CD004587).

5. Electrolytes added to prophylactic gel media for electrical conductive gels used for catheter tip position and ECG electrode attachment.

Dual Needle Apparatus

The dual needle apparatus of the present invention is somewhat similar to the Dialock needle configuration shown in FIG. 2. The dual needle apparatus of the present invention differs by comprising non-cutting needles for coupling to the new port 4, including a bendable trocar member 25 preferably constructed of plastic, and a trocar tip that is blunt and capable of separating tissue rather than cutting during passage through tissue. The new dual needle assembly incorporates a "ball" or "plug" valve 29, which is useful for sealing off the circuit to an external machine (e.g., an HD machine). The dual needle apparatus further eliminates the flexible tubing portion included in the prior art design, thereby eliminating two failure modes from the prior Dialock needle (i.e., a flexible tube that was clamped with the trocar in place and tubing that was not straight when the trocar was inserted). Each case caused lost seal integrity and blood leakage. The new needle assembly comprises a non luer lock connection to mate with a new, optimized blood line design, to achieve redundancy against a "single fault" break in the needle/blood line connection and improved blood flow dynamics.

Optimized Ancillary Bloodline

The present invention envisions one piece construction of an external blood circuit comprising port needles, blood lines which incorporates a portion to engage the blood flow driving apparatus (i.e., the peristaltic rollers of an HD machine or other type of driver which produces flow in a tube) and the dialyzer. This assembly is preferably sterilizable, and reusable, so that it may be used for several HD sessions. It preferably comprises attachment means for attachment to the HD machine, including a dialysate circuit. It may comprise means for maintaining attachment to the HD machine during the cleaning and sterilization cycle. It is anticipated that a special home sterilizer will allow easy home sterilization, under automatic control, so as to subject the patient to less cumbersome sterilization methods. Home dialysis patients are exposed to substantially fewer risks from virulent microbes, such as hepatitis, AIDS or other common healthcare infections, which are commonly found in patients treated in HD clinics. Accordingly, reuse of some "single-use" medical components is appropriate for the home environment, particularly when the patient is spared tasks. Furthermore, such a design provides good fluid design practice and eliminates flow perturbations and dead flow zones which occur in prior fluid connections between components designed for disconnection. The system further increases the savings inherent in home HD.

New HD machines for nocturnal HD or "Wearable" HD operate with lower blood flow rates enable smaller bore blood lines. Current HD blood lines are standardized for short HD times based on Kt/V criteria and require a high rate of HD blood flow. Home HD may operate at lower blood flow rate and bloodlines designed for the lower flow rate may achieve improved performance and health benefits, which are enhanced by self-accessing. The present invention includes a new blood line that is easier to use and lowers inherent costs significantly.

The Bloodline changes over prior bloodlines comprise:

1. Replacement of the standard luer connector between the needle 5 and the blood line 33 allows for a smooth fluid flow path and secure connection between the needles 5 and blood line 33. The connection tolerates some axial movement, without blood spillage. Current luer connections can cause serious blood leakage from slight loosening of the luer screw connection. The HD needle assembly incorporates a connection locking feature to couple the needle to the bloodline, which eliminates "single fault" failure from inadvertent disconnection. A smooth bore eliminates the major flow perturbation in the blood line/patient interface and reduces harmful high blood flow effects (i.e., platelet activation, hemolysis and thrombosis).

2. Smaller bore blood lines, which are less cumbersome for patient connection and enable neat draping of blood lines during HD, offer easier cleaning between uses.

3. Blood lines capable of multiple HD sessions.

4. Another option is to incorporate pressure transducers directly into the blood lines system for smooth air free flow path.

5. Option to eliminate flow or drip chambers 20 which cause blood damage.

Experimental Data

Septum Puncturing Life Testing

Evaluation of septum closure and sealing integrity was performed with a variety of septa and needle types, seeking to find a combination enabling extended puncture life when subjected to large HD needle diameters. Different combinations of rubber compositions, compression stresses and tip configuration test specimens typical to conventional septum port use were subjected to randomly spaced puncture life testing. The results clearly demonstrate that the standard port septum configuration is not compatible with large diameter needle puncturing, which cuts the rubber during each penetration. Analysis of the failures of standard port septa and further testing has led to the concept of the present invention for the use of blunted non-cutting, conical tip trocar needles punctured exactly through the same line in the septum (i.e., through puncture line 22) and lubricated for long puncture life (i.e., greater than 10,000 punctures without leakage and without generating wear particles).

However, large sharply pointed conical needles are not acceptable for repeated piercing of subcutaneous tissue (i.e., because such repeated piercing causes extreme trauma to subcutaneous tissue and creates healing complications). This suggests that use of a BH tract may enable penetration through tissue with blunted needles. However, Lifesite experienced severe complications with the use of a BH. Other, more recent data, also indicates increased rate of infections and/or severity when associated with BH/AVF applications. Furthermore, our testing revealed that some configurations of blunted large needles damage the septum in single path penetration by "shaving" of septum material, and generate wear particles which can cause contamination.

Subcutaneous Tissue Prophylaxis

Clinical testing of methods to treat, or prevent, infections in tissue traumatized by needle puncturing of a Dialock port was undertaken during a European trial. Injection of an antimicrobial liquid taurolidine "lock" into the tissue capsule surrounding the port, and into the port entrance and needle tract, was found to be safe and efficacious treatment for preventing infection of these sites, as well as being a good prophylactic procedure in the needle tract and subcutaneous tissue adjacent to Dialock.

Other clinical evaluations performed using a conventional BH technique, in conjunction with a Dialock port and a liquid taurolidine "lock" revealed that a BH tract could be protected against infection by instilling an antimicrobial liquid "lock" solution into a BH tract during needle withdrawal, after the HD session, thereby supporting the idea that a tract through tissue (such as a BH) may enable blunt needle passage, and, combined with a single puncture path septum closure, may further protect the patient against infection.

The biocompatible gel (Polaschegg EP1442753) maintains itself within the tract and catheter lumen rather than spilling out, and is further enhanced by incorporating a lubricating action, which provides the critical characteristic necessary to achieve long puncture-life for the septum, and further facilitates needle passage through the tissue tract.

Gel Testing

A gel for use as a catheter lock prophylaxis was evaluated to determine the necessary rheology characteristics suitable for a catheter lock. It was determined that a viscoelastic material is necessary with the following properties:
 1. Plug flow characteristic through an HD needle and catheter rather than the laminar flow profile of Newtonian fluids, enabling complete filling of the entire internal catheter volume without spilling, by injection of a volume equal to the catheter volume;
 2. "die swelling" behavior enabling the gel to contact the entire luminal surface of the catheter where Biofilm forms when injected from a typical medical syringe;
 3. shear yield strength and viscosity values enabling instillation and withdrawn of the gel from catheter/port's inner space in a timely manner;
 4. shear yield strength sufficient to provide redundant sealant capability against loss of the gel within the catheter or the tissue tract so as to prevent blood loss or air egress and block blood from entering catheter between access;
 5. tensile strength of gel to maintain a single cohesive mass for ease of aspirating;
 6. ability to return to an original solid-like state when stain rate reduces to zero;
 7. residual coating of the gel layer on luminal surfaces after expulsion of gel from luminal spaces;
 8. gel solubilizes in blood.

Experiments with catheters and locking solutions elucidate factors causing flow degradation and the biofilm formation in long term catheter. (Polaschegg HD. Catheter locking solution spillage: theory and experimental verification. Blood Purif 2008; 26:255-60; Polaschegg HD. Physics of Catheter Locking Solutions. Dialysis Times 2005; 10:1, 3-6; Polaschegg HD. Loss of Catheter Locking Solution Caused by Fluid Density. ASAIO J 2005; 51:230-5) is the basis for the invention of the Gel Lock (Polaschegg 20040156908).

Conventional liquid catheter locks spill approximately 25% of the amount instilled into the blood circulation of the patient during the instillation. Subsequent spillage occurs over several minutes or hours as blood is exchanged with the lock solution, driven by density differences between blood and lock solution. For example, if a lock solution has a higher density than the blood of the patient, such as concentrated trisodium citrate (30% or 46.7%), the exchange of the "lock" occurs within minutes in HD catheters. Loss of the "lock" within the catheter, comprising an active pharmaceutical agent (API) such as heparin or biocide, deprives a patient of the assumed protection from infection, clotting, etc. This clarifies why locks fail to work even with an API concentration that substantially exceeds the desired level of protection. For example, it was commonly observed that extremely high concentration heparin locks fail to provide anti-clotting protection within a catheter.

This invention applies gel "lock" prophylaxis to a novel tissue tract, and utilizes added lubricious attributes of the gel "lock" to enable a simpler and more reliable HD port, thereby satisfying the requirements of large needle coupling to the port and ensures long access puncture life of the septum of the port. Gel locks may be formulated to provide redundant sealing and to prevent blood losses or air ingestion in the event of a primary septum closure failure.

Catheter Diffusion Experiment

The inventors observed, during Biolink's port trials, that conventional silicone rubber catheters, locked with taurolidine, remained pristine white after many months of implantation. However heparin-locked catheters, when subjected to similar conditions, became stained a visible light brownish color. It was hypothesized that taurolidine locks protect the catheter from being coated with blood products. The inventors performed tests verifying that taurolidine indeed does pass through the silicone of a silicone rubber catheter. Silicone elastomers characteristically show high diffusion rates for many fluids, such as alcohol and other small molecules. Accordingly, these prophylactic "lock" compositions may also provide prophylaxis for the outer surface of polymers catheters when used as a lock, which acts as a reservoir depot for the APA.

Needle Insertion into Port Aperture

It was found, during the first animal experiments evaluating an early port design, that it was extremely difficult to pierce tissue and to insert a large conical pointed sharp needle (i.e., 15 gauge size) into an implanted port when the port utilized a funnel-shaped lead-in designed for guiding the needle to the center of the aperture passage. Three-sided trocar tip (i.e., 3 cutting edges) needles were still too difficult for patient use as demonstrated in cadaver tests. It was learned that, during insertion, epidermis tissue was pushed into the funnel space between needle OD and the aperture, blocking (or jamming) the needle so that the needle could not enter the aperture, even after high force was applied.

Patent References

Port, Septum and Catheter Locks

1. U.S. Pat. No. 3,731,681, Blackshear, IMPLANTABLE INFUSION PUMP
2. U.S. Pat. No. 4,417,888, Renal System (Assignee) Percutaneous Implant
3. U.S. Pat. No. 4,543,088 American Hospital Supply Corp. (Assignee) Self-sealing subcutaneous injection site
4. U.S. Pat. No. 4,673,394, Fenton, Implantable Treatment Reservoir
5. U.S. Pat. No. 4,014,328, Cluff, Blood Sampling and infusion chamber
6. U.S. Pat. No. 4,190,040 American Hospital Supply Corp (Assignee) Resealable puncture housing for surgical implantation
7. U.S. Pat. No. 400,169 Stephen, Subcutaneous peritoneal injection catheter
8. U.S. Pat. No. 4,445,896 Cook, Inc. Catheter plug
9. U.S. Pat. No. 4,490,137 Moukheibir, Surgically implantable peritoneal dialysis apparatus,
10. U.S. Pat. No. 4,569,675 Prosl, Transcutaneous infusion system
11. U.S. Pat. No. 4,581,020, Mittleman, Medication delivery device and system for percutaneous administration of medication
12. U.S. Pat. No. 4,692,146, Hilger, Multiple vascular access port
13. U.S. Pat. No. 4,704,103, Stober, Implantable catheter means
14. U.S. Pat. No. 4,710,167, Lazorthes, Implantable device for chronically injecting a substance, in particular a therapeutant
15. U.S. Pat. No. 4,710,174, Moden, Implantable infusion port
16. U.S. Pat. No. 4,781,680, Redmond, Resealable injection site
17. U.S. Pat. No. 4,781,695, Dalton, Implantable fluid dispenser
18. U.S. Pat. No. 4,790,826, Elftman Percutaneous access port
19. U.S. Pat. No. 4,832,054, Bark, Septum
20. U.S. Pat. No. 4,857,053, Dalton, Matrix septum
21. U.S. Pat. No. 4,496,343, Prosl, Infusate pump
22. U.S. Pat. No. 4,978,338, Melsky, Implantable infusion apparatus
23. U.S. Pat. No. 5,041,098 Loiterman, Vascular access system for extracorporeal treatment of blood
24. U.S. Pat. No. 5,092,849, Sampson, Implantable device
25. U.S. Pat. No. 5,226,879, Ensminger, Implantable access device
26. U.S. Pat. No. 5,520,643, Ensminger, Implantable access devices
27. U.S. Pat. No. 5,281,199, Ensminger, Implantable access devices
28. U.S. Pat. No. 5,318,545, Tucker, Composite implantable biocompatible vascular access port device
29. U.S. Pat. No. 5,336,194, Polaschegg, Implantable apparatus
30. U.S. Pat. No. 5,417,656, Ensminger, Implantable access devices
31. U.S. Pat. No. 5,704,915, Melsky, Hemodialysis access device
32. U.S. Pat. No. 5,755,780, Finch, Implantable vascular device
33. U.S. Pat. No. 5,911,706, Estabrook, Device for subcutaneous accessibility
34. U.S. Pat. No. 5,954,691, Prosl, Hemodialysis access apparatus
35. U.S. Pat. No. 5,989,206, Prosl, Apparatus and method for the dialysis of blood
36. U.S. Pat. No. 5,989,239, Finch, Method and apparatus for percutaneously accessing an implanted port
37. U.S. Pat. No. 6,007,516, Burbank, Valve port and method for vascular access
38. U.S. Pat. No. 6,013,058, Prosl, Device for subcutaneous accessibility
39. U.S. Pat. No. 6,120,492, Finch, Method and apparatus for percutaneously accessing an implanted port
40. U.S. Pat. No. 6,206,851, Prosl, Hemodialysis access apparatus
41. U.S. Pat. No. 6,352,521, Prosl, Valve and sealing means for hemodialysis access device
42. U.S. Pat. No. 6,451,003 Prosl Method for overcoming infection in tissue pocket surrounding implanted device
43. U.S. Pat. No. 7,131,962, Estabrook, Port device for subcutaneous access to the vascular system of a patient
44. U.S. Pat. No. 6,436,089, Danielson, Connecting device for medical purposes
45. 2005020957, Brugger Method and apparatus for percutaneously accessing a pressure activated implanted port
46. US20100166102, Ziebol, Apparatus for Delivery device and Antimicrobial Agent into Trans-Dermal Catheter
47. 20080027043 Herdeis PREPARATION OF ANTIMICROBIAL FORMULATIONS USING 7-OXA-2-THIA-1,5-DIAZABICYCLO [3.3.1]NONANE-2,2-DIONE
48. U.S. Pat. No. 6,451,003, Prosl, Method and Apparatus for overcoming infection in tissue pocket surrounding implanted device
49. U.S. Pat. No. 5,057,084 Ensminger, Implantable Infusion Devices
50. U.S. Pat. No. 5,180,365, Ensminger, Implantable Infusion Devices
51. U.S. Pat. No. 5,226,879 Ensminger, Implantable Infusion Devices
52. U.S. Pat. No. 5,281,199, Ensminger, Implantable Infusion Devices
53. U.S. Pat. No. 5,350,360, Ensminger, Implantable Infusion Devices
54. U.S. Pat. No. 5,356,381, Ensminger, Implantable Infusion Devices
55. U.S. Pat. No. 5,417,656. Ensminger, Implantable Infusion Devices
56. U.S. Pat. No. 5,476,451, Ensminger, Implantable Infusion Devices
57. U.S. Pat. No. 5,503,630, Ensminger, Implantable Infusion Devices 58. U.S. Pat. No. 5,520,643, Ensminger, Implantable Infusion Devices 59. U.S. Pat. No. 5,527,277, Ensminger, Implantable Infusion Devices 60. U.S. Pat. No. 5,527,278, Ensminger, Implantable Infusion Devices 61. U.S. Pat. No. 5,531,684, Ensminger, Implantable Infusion Devices Device Prophylaxis Gels 62. 20080177217, Polaschegg, Taurolidine Formulations and Delivery: Therapeutic Treatments and Antimicrobial Protection Against Bacterial Biofilm Formation 63. 20050042240, Utterberg, High viscosity antibacterials 64. 20030144362, Utterberg, High viscosity antibacterials for cannulae 65. 20060024372, Utterberg, High viscosity antibacterials 66. U.S. Pat. No. 4,337,251 Pfirrmann, Method of Avoiding and Removing Adhesions 67. 20040156908 Polaschegg, Prevention of indwelling device related infection: composition and methods

What is claimed is:

1. A method for surgically inducing tissue tract formation, comprising:
   a. determining patient preferences for accessing and vascular conditions;
   b. inserting a catheter using the Seldinger technique using usual practice and establish a correct position of the catheter tip in right atrium of the patient using an imaging technique;
   c. testing flow patency during instillation and withdrawal of fluid, and fixing the catheter near the insertion site of vessel;
   d. creating a pocket for a port, and verifying size;
   e. creating a tunnel from the insertion site of the catheter to the pocket;
   f. inserting a piercing tool, retrograde, through integral port tubes which are catheter attachment points and pushing the piercing tool so as to enter the port passage and penetrate a septum of the port but not exit the other end of the port passage;
   g. positioning the port in the pocket and suturing the port to underlying fascia using suture sites integral with a housing of the port;
   h. positioning skin and subcutaneous tissue which is wide open into a position it will take after pocket closure and restrain the skin and subcutaneous tissue with temporary means;
   i. continuing insertion of the piercing tool such that it exits the port and advances through the subcutaneous tissue in a line projected from the port's entrance aperture and penetrates the patient's epidermis and protrudes from the skin;
   j. removing the piercing tool and inserting a foreign body platform tool along the pierced path just created and passing a probe end of the tool into the port's aperture as completely allowed;
   k. positioning the wings of the tool such that the flat surface is in an orientation, with minimal tensile stress, to minimize an opening tendency of a created tract in local subcutaneous tissue;
   l. cutting the catheter to correct length and attaching the catheter to the port body;
   m. fixing the foreign body tool temporarily in this position outside the body;
   n. closing the pocket;
   o. removing the "foreign body" tool and flushing the port/catheter with antimicrobial lock solution;
   p. replacing the "foreign body" tool and fixing it in place and applying an antimicrobial dressing; and
   q. maintaining in a clean condition for approximately 1 week to allow for the tissue tract formation if hemodialysis is required sooner, repeat steps o. and n. to allow for needle coupling with the port to provide access for hemodialysis treatment and subsequently reinsert the foreign body tool to enable fuller tract formation.

2. A method according to claim 1 wherein the catheter and a tubular conduit form a needle assembly which couples to the port by insertion of the needle assembly along the tunnel and into the port, wherein the needle assembly is mechanically stopped at a proper docking position, thereby creating an open transcutaneous flow path from the exterior of the patient to the vasculature of the patient.

3. A method according to claim 2 further comprising providing a lock mechanism for engaging the needle assembly so as to hold the needle assembly within the port after insertion of the needle assembly into the port.

4. A method according to claim 2 wherein the tissue tract guides insertion of the needle assembly to engage precisely with the port.

5. A method according to claim 2 wherein the antimicrobial lock solution comprises a gel composition providing antimicrobial action and lubrication action, wherein the antimicrobial lock solution can be instilled within the port blood passage and the tissue tract during the disconnection procedure after hemodialysis treatment, such that the antimicrobial lock solution protects against microbial colonization within the blood pathway and the tissue tract, whereby to prevent bloodstream and subcutaneous tissue infections and whereby to also provide easy penetration of the needle assembly along the tissue tract during subsequent docking of the needle assembly with the port.

6. A method according to claim 2 wherein the port comprises a housing having an internal passage passing therethrough, wherein the septum seals the distal end of the internal passage from the proximal end of the internal passage, wherein the port further comprises means for connecting the distal end of the internal passage with the catheter, and a mechanical stop which blocks the needle assembly insertion beyond the correct position, wherein the mechanical stop provides tactile feedback during insertion of the needle assembly.

7. A method according to claim 6 wherein the port comprises a valve closure comprising the septum installed and positioned in the internal passage, wherein the needle assembly is configured to pass through the septum precisely, in a single path coincident with one or more intersecting slits formed in the septum, and further wherein the needle assembly comprises a non-cutting blunted tip which separates the one or more intersecting slits as the needle passes through the one or more slits without damaging the septum, until the needle assembly reaches the mechanical stop, whereby to provide exceptional puncture life to the port septum.

8. A method according to claim 7 wherein the one or more slits are produced by at least one technique selected from the group consisting of mechanical cutting, molding in place and laser cutting.

9. A method according to claim 6 wherein the housing comprises a feature on its outer surface similar to tube bead geometry disposed around the port passage, whereby to allow the tissue tract to form and become fixed to the housing in coincident alignment with the port passage.

10. A method according to claim 9 wherein the feature on the outer surface of the port housing comprises a tissue anchor formed around an opening in the port housing, the tissue anchor comprising means for anchoring one end of a tissue tract to the port housing so that the tissue tract is aligned with the opening.

11. A method according to claim 6 wherein the housing comprises a shape and surface which is configured to facilitate tight membrane tissue encapsulation formation around the housing and to conjoin with the tissue tract.

12. A method according to claim 6 wherein the housing comprises an aspect ratio which minimizes tensile stress in the epidermis and subcutaneous tissue and further wherein the housing comprises means to secure the housing to the body of a patient so as to minimize relative displacement between the tissue tract and the port.

13. A system according to claim 6 wherein the housing comprises two internal passages, wherein one of the two internal passages comprises a blood withdrawal circuit and the other of the two internal passages comprises a blood return circuit with one end of each internal passage connected to the catheter, and further wherein the port comprises means which enable lower blood flow through the catheter and each internal passage, whereby to improve patency and provide a means to overcome bleed out from needle dislodgement.

14. A method according to claim 2 wherein the needle assembly comprises a stiff hyperemic cannula, a housing, and a flexible fiber-like rod having a rounded or conical shaped distal tip which can enter the cannula and protrude from the distal end thereof and be locked in place, such that during insertion of the needle assembly into the tissue tract, the rounded or conical shaped distal tip acts to spread apart the tissue tract without cutting as the needle assembly passes through the tract, whereby to prevent bleeding or pain to the patient.

15. A method according to claim 1 wherein the septum comprises an opening, the septum being held in the port under compression so as to normally close off the opening.

16. A method according to claim 1 wherein the port comprises means for releasably locking a hemodialysis needle to the port.

17. A method according to claim 1 wherein a biocidal lock is disposed in the catheter between the septum and the vascular structure.

18. A method according to claim 1 wherein a biocidal lock is disposed in the tissue tract between the septum and the surface of the skin.

19. A method according to claim 18 wherein the tissue tract is selectively closed adjacent to the surface of the skin.

20. A method according to claim 19 wherein the tissue tract is selectively closed with a bandage.

21. A method according to claim 1 wherein the tissue tract is in the form of a slit.

* * * * *